US012642596B2

(12) United States Patent
Sexson et al.

(10) Patent No.: US 12,642,596 B2
(45) Date of Patent: Jun. 2, 2026

(54) NAVIGATIONAL AND/OR ROBOTIC TRACKING METHODS AND SYSTEMS

(71) Applicant: Monogram Orthopaedics Inc., Austin, TX (US)

(72) Inventors: Benjamin Sexson, Austin, TX (US); Hrisheekesh Patil, Austin, TX (US)

(73) Assignee: Zimmer, Inc., Warsaw, IN (US)

( * ) Notice: Subject to any disclaimer, the term of this patent is extended or adjusted under 35 U.S.C. 154(b) by 127 days.

(21) Appl. No.: 18/064,732

(22) Filed: Dec. 12, 2022

(65) Prior Publication Data

US 2023/0111411 A1      Apr. 13, 2023

Related U.S. Application Data

(63) Continuation of application No. PCT/US2021/036985, filed on Jun. 11, 2021.

(Continued)

(51) Int. Cl.
*A61B 34/00*        (2016.01)
*A61B 8/00*        (2006.01)
(Continued)

(52) U.S. Cl.
CPC ............ *A61B 34/20* (2016.02); *A61B 8/4245* (2013.01); *A61B 8/4472* (2013.01); *A61B 34/32* (2016.02);
(Continued)

(58) Field of Classification Search
CPC ...................................................... A61B 34/20
See application file for complete search history.

10⟶

(56) References Cited

U.S. PATENT DOCUMENTS

2008/0312530 A1    12/2008   Malackowski et al.
2010/0168562 A1     7/2010   Zhao et al.
(Continued)

FOREIGN PATENT DOCUMENTS

JP        2016512084 A      4/2016
JP        2019523664 A      8/2019
(Continued)

OTHER PUBLICATIONS

International Preliminary Report on Patentability for International Application No. PCT/US2021/036985 dated Dec. 13, 2022, 20 pages, International Bureau of WIPO.
(Continued)

*Primary Examiner* — Joseph M Santos Rodriguez
(74) *Attorney, Agent, or Firm* — SCHWEGMAN LUNDBERG & WOESSNER, P.A.

(57) ABSTRACT

Navigational and/or robotic tracking systems include one or more wireless tracking device attached to an object or to a bone of a patient. The wireless tracking device may include a camera, a pair of cameras, and/or a probe, and a wireless transmitter. Surgical methods may include wirelessly obtaining reference data, the reference data based on the camera of the wireless tracking device operably attached to the bone of the patient, the reference data is associated with a plurality of markers and using the reference data in a surgical navigation system. Surgical methods may also include wirelessly obtaining positional and orientation data, and/or surface or structural data, and using the positional and orientation data, and/or surface or structural data in the surgical navigation system.

25 Claims, 19 Drawing Sheets

Related U.S. Application Data

(60) Provisional application No. 63/037,699, filed on Jun. 11, 2020.

(51) Int. Cl.

| | |
|---|---|
| *A61B 34/20* | (2016.01) |
| *A61B 34/32* | (2016.01) |
| *A61B 90/00* | (2016.01) |
| *G06T 7/00* | (2017.01) |
| *G06T 7/292* | (2017.01) |
| *G06T 7/38* | (2017.01) |

(52) U.S. Cl.
CPC ............ *A61B 34/70* (2016.02); *A61B 90/361* (2016.02); *A61B 90/39* (2016.02); *G06T 7/0012* (2013.01); *G06T 7/292* (2017.01); *G06T 7/38* (2017.01); *A61B 2034/2057* (2016.02); *A61B 2034/2063* (2016.02); *A61B 2034/2065* (2016.02); *A61B 2034/2068* (2016.02); *G06T 2207/30008* (2013.01)

(56) References Cited

U.S. PATENT DOCUMENTS

| | | |
|---|---|---|
| 2014/0052149 A1 | 2/2014 | van der Walt et al. |
| 2016/0256225 A1 | 9/2016 | Crawford et al. |
| 2018/0064496 A1 | 3/2018 | Hladio et al. |
| 2018/0064497 A1 | 3/2018 | Hussain et al. |
| 2018/0132945 A1 | 5/2018 | Fazzi |
| 2018/0256145 A1 | 9/2018 | Tesar et al. |
| 2018/0256259 A1 | 9/2018 | Crawford |
| 2019/0090955 A1 | 3/2019 | Singh et al. |
| 2019/0142527 A1 | 5/2019 | Andersson |
| 2019/0380792 A1 | 12/2019 | Poltaretskyi et al. |
| 2020/0159313 A1 | 5/2020 | Gibby et al. |

FOREIGN PATENT DOCUMENTS

| | | |
|---|---|---|
| WO | 2014200017 A1 | 6/2014 |
| WO | 2017151734 A1 | 9/2017 |
| WO | 2017157763 A1 | 9/2017 |
| WO | 2017218928 A1 | 12/2017 |
| WO | 2018063528 A1 | 4/2018 |
| WO | 2018150336 A1 | 8/2018 |
| WO | 2019087904 A1 | 5/2019 |
| WO | 2019136412 A1 | 7/2019 |
| WO | 2021252882 | 12/2021 |

OTHER PUBLICATIONS

Extended European Search Report for EP Application No. 21822323.8, mailed on May 29, 2024, 7 pages, May 29, 2024.

International Search Report and Written Opinion of the International Searching Authority for International Application No. PCT/US2021/036985 (published as WO2021/252882), 22 pages, mailed on Sep. 29, 2021.

Antilatency Tracker, available from Guangzhou Alt Technology Limited, Guangzhou, China, printout retrieved on Dec. 12, 2022, at https://antilatency.com/, (Wayback Verification Crawl Presence dated Jul. 7, 2019), 10 pages, Jul. 7, 2019.

Monogram Orthopaedics Inc., Japanese Final Office Action mailed Nov. 4, 2025, Japanese Patent Application No. 2022-576558, 7 pages, Nov. 4, 2025.

Monogram Orthopaedics Inc., Japanese First Office Action mailed Jan. 21, 2025, Japanese Patent Application No. 2022-576558, 18 pages, Jan. 21, 2025.

Monogram Orthopaedics Inc., Australian Examination Report mailed Aug. 5, 2025, Australian Patent Application No. 2021288205, 3 pages, Aug. 5, 2025.

Monogram Orthopaedics Inc., European Patent Examinatoin Report mailed Sep. 22, 2025, European Patent Application No. 21822323.8, 5 pages, Sep. 22, 2025.

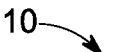
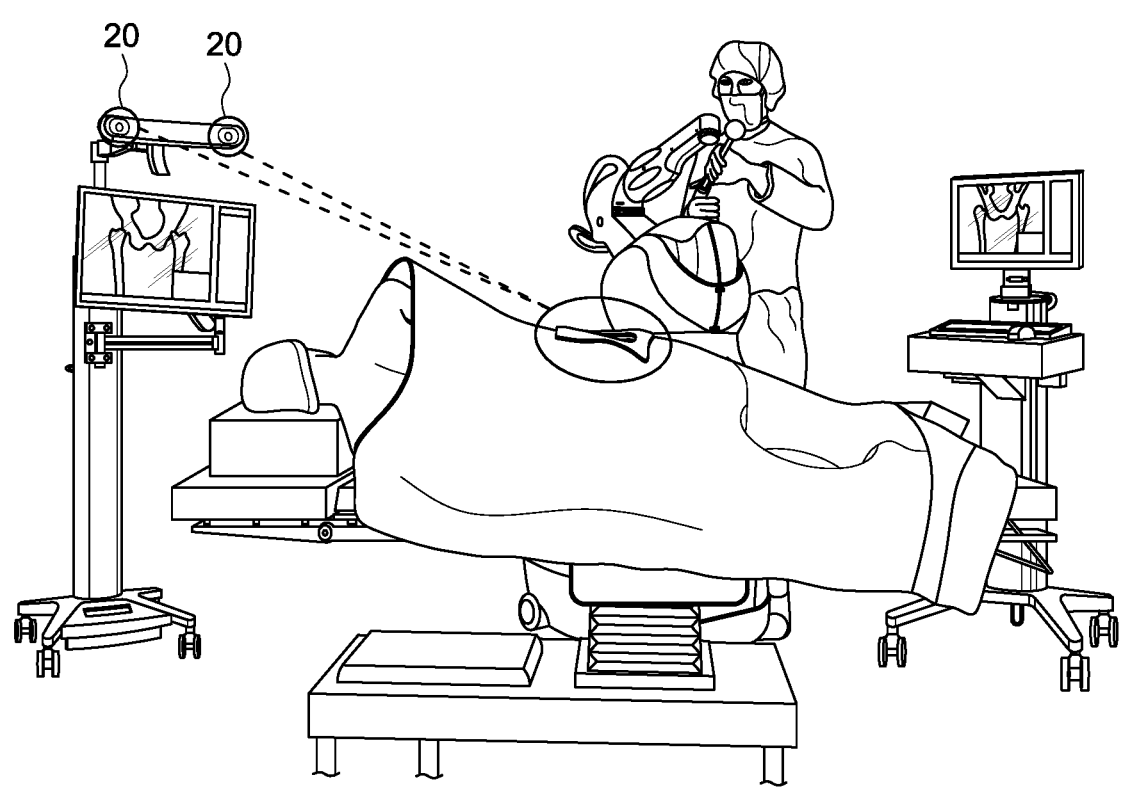
FIG. 1
(Prior Art)

1000

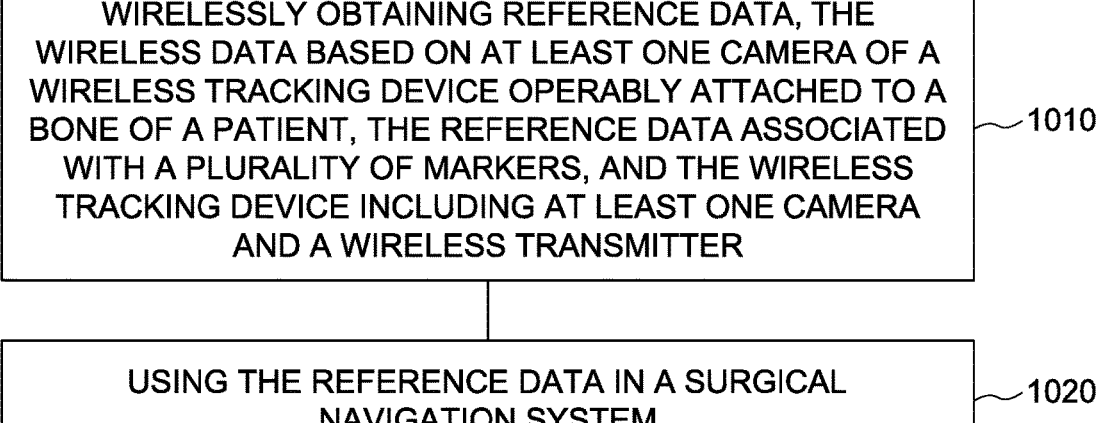

WIRELESSLY OBTAINING REFERENCE DATA, THE WIRELESS DATA BASED ON AT LEAST ONE CAMERA OF A WIRELESS TRACKING DEVICE OPERABLY ATTACHED TO A BONE OF A PATIENT, THE REFERENCE DATA ASSOCIATED WITH A PLURALITY OF MARKERS, AND THE WIRELESS TRACKING DEVICE INCLUDING AT LEAST ONE CAMERA AND A WIRELESS TRANSMITTER — 1010

USING THE REFERENCE DATA IN A SURGICAL NAVIGATION SYSTEM — 1020

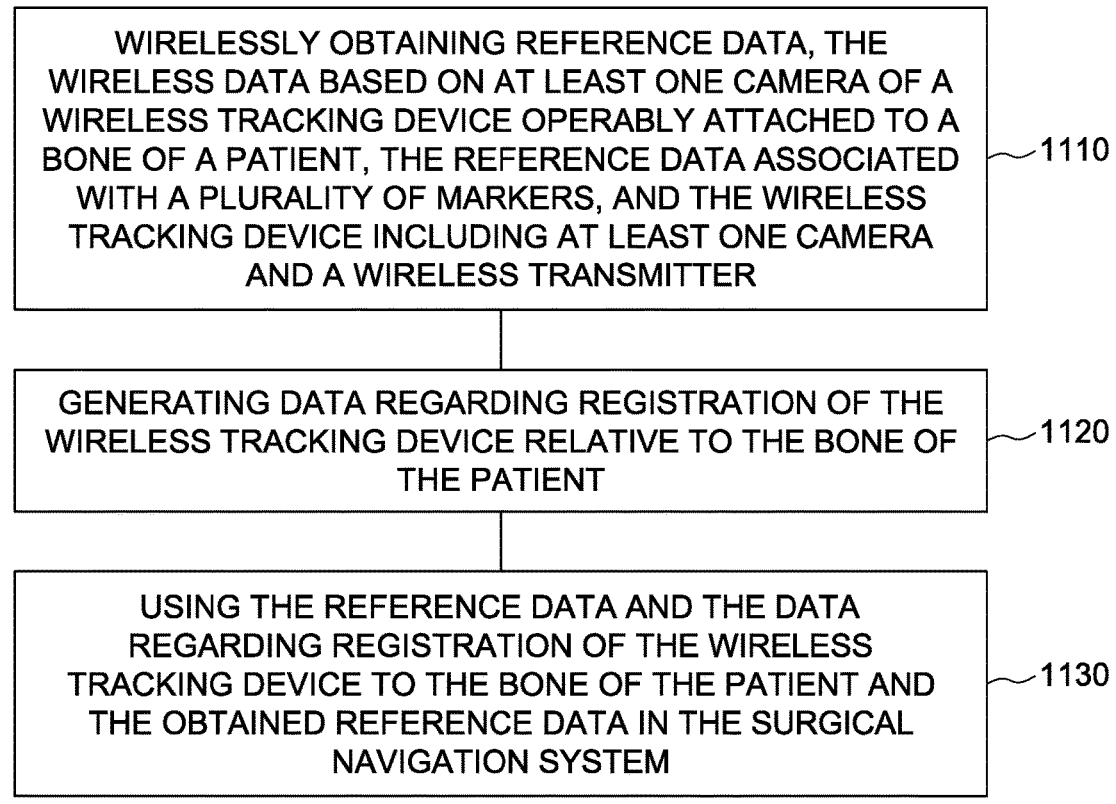

WIRELESSLY OBTAINING REFERENCE DATA, THE WIRELESS DATA BASED ON AT LEAST ONE CAMERA OF A WIRELESS TRACKING DEVICE OPERABLY ATTACHED TO A BONE OF A PATIENT, THE REFERENCE DATA ASSOCIATED WITH A PLURALITY OF MARKERS, AND THE WIRELESS TRACKING DEVICE INCLUDING AT LEAST ONE CAMERA AND A WIRELESS TRANSMITTER ⏤1110

GENERATING DATA REGARDING REGISTRATION OF THE WIRELESS TRACKING DEVICE RELATIVE TO THE BONE OF THE PATIENT ⏤1120

USING THE REFERENCE DATA AND THE DATA REGARDING REGISTRATION OF THE WIRELESS TRACKING DEVICE TO THE BONE OF THE PATIENT AND THE OBTAINED REFERENCE DATA IN THE SURGICAL NAVIGATION SYSTEM ⏤1130

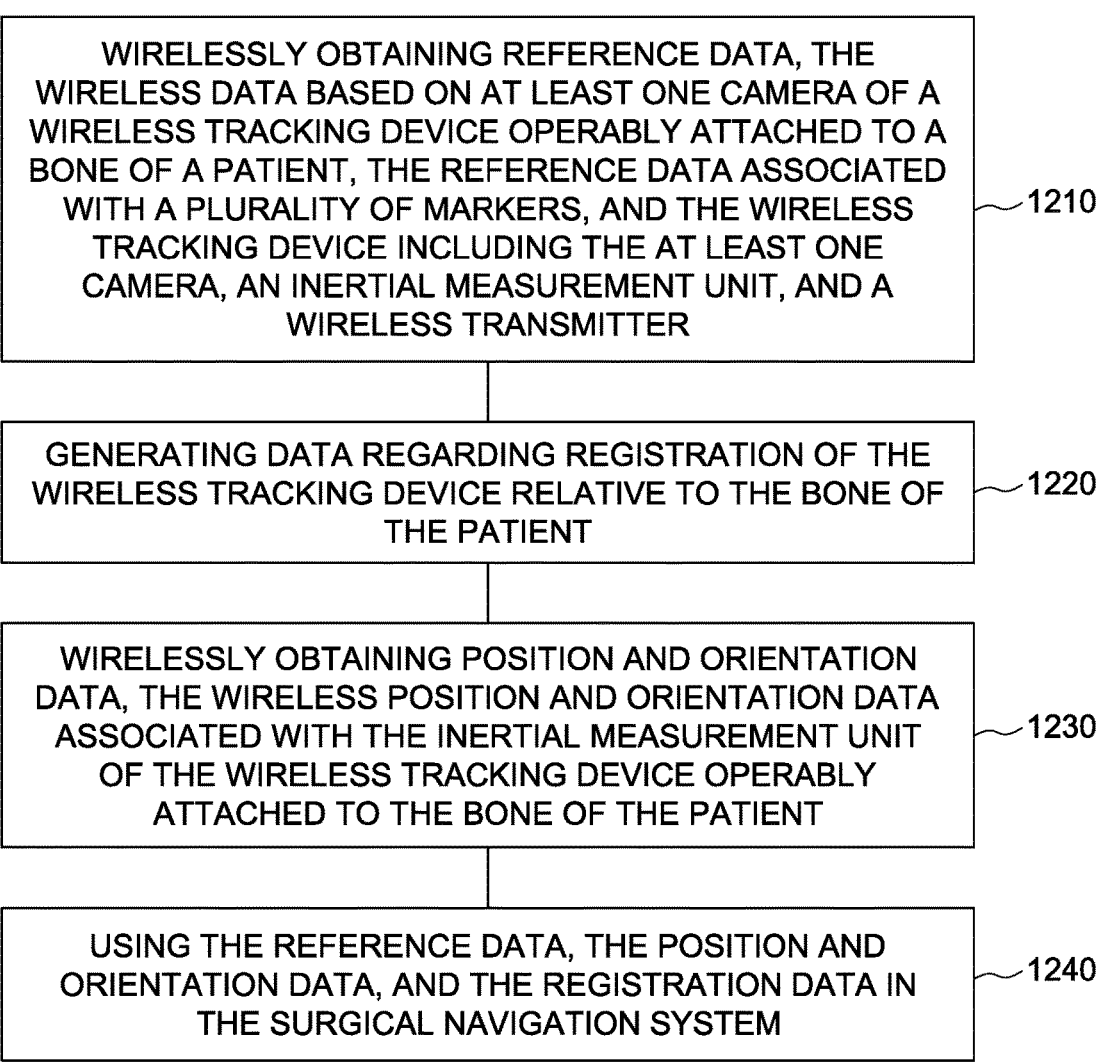

WIRELESSLY OBTAINING REFERENCE DATA, THE WIRELESS DATA BASED ON AT LEAST ONE CAMERA OF A WIRELESS TRACKING DEVICE OPERABLY ATTACHED TO A BONE OF A PATIENT, THE REFERENCE DATA ASSOCIATED WITH A PLURALITY OF MARKERS, AND THE WIRELESS TRACKING DEVICE INCLUDING THE AT LEAST ONE CAMERA, AN INERTIAL MEASUREMENT UNIT, AND A WIRELESS TRANSMITTER — 1210

GENERATING DATA REGARDING REGISTRATION OF THE WIRELESS TRACKING DEVICE RELATIVE TO THE BONE OF THE PATIENT — 1220

WIRELESSLY OBTAINING POSITION AND ORIENTATION DATA, THE WIRELESS POSITION AND ORIENTATION DATA ASSOCIATED WITH THE INERTIAL MEASUREMENT UNIT OF THE WIRELESS TRACKING DEVICE OPERABLY ATTACHED TO THE BONE OF THE PATIENT — 1230

USING THE REFERENCE DATA, THE POSITION AND ORIENTATION DATA, AND THE REGISTRATION DATA IN THE SURGICAL NAVIGATION SYSTEM — 1240

FIG. 16

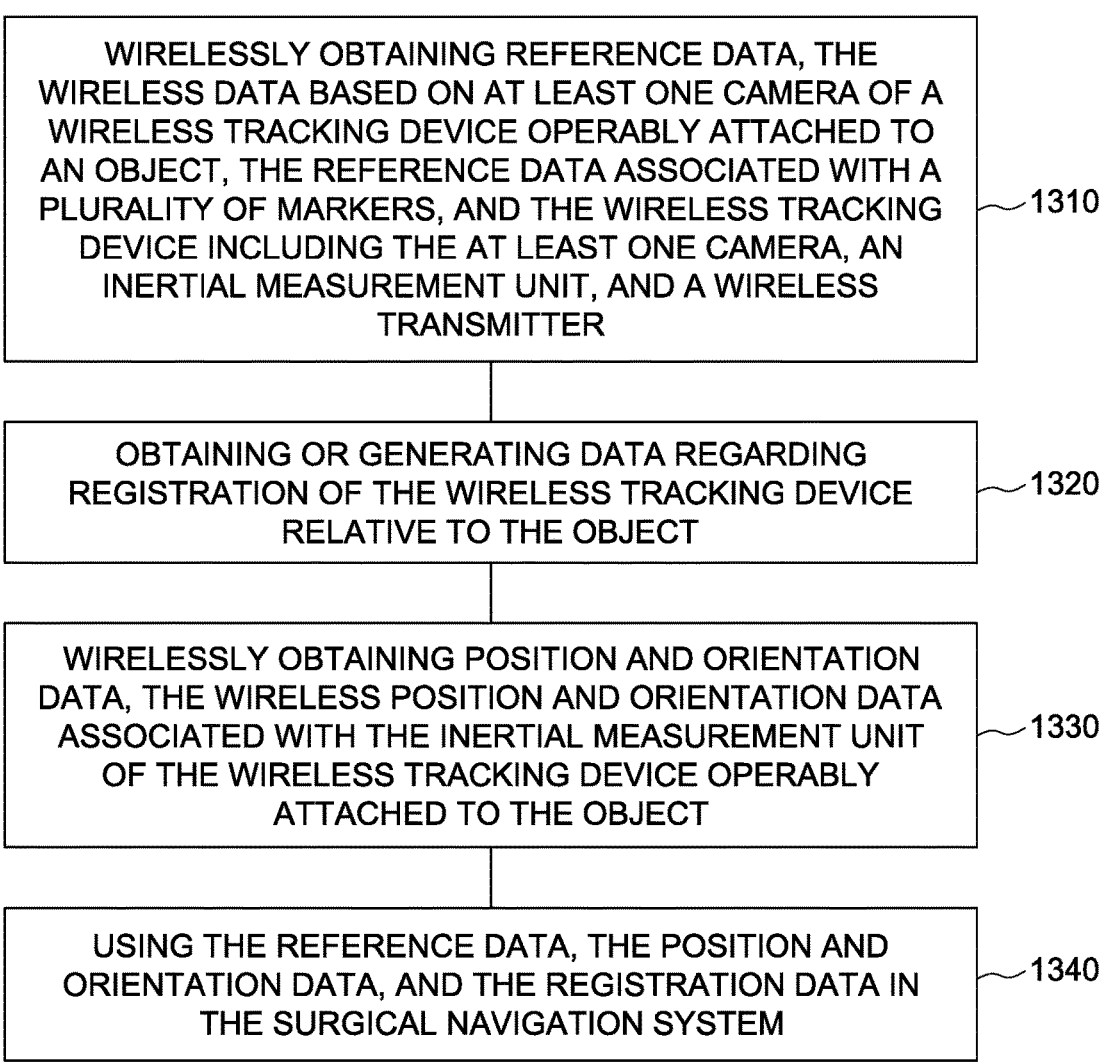

1300

WIRELESSLY OBTAINING REFERENCE DATA, THE WIRELESS DATA BASED ON AT LEAST ONE CAMERA OF A WIRELESS TRACKING DEVICE OPERABLY ATTACHED TO AN OBJECT, THE REFERENCE DATA ASSOCIATED WITH A PLURALITY OF MARKERS, AND THE WIRELESS TRACKING DEVICE INCLUDING THE AT LEAST ONE CAMERA, AN INERTIAL MEASUREMENT UNIT, AND A WIRELESS TRANSMITTER — 1310

OBTAINING OR GENERATING DATA REGARDING REGISTRATION OF THE WIRELESS TRACKING DEVICE RELATIVE TO THE OBJECT — 1320

WIRELESSLY OBTAINING POSITION AND ORIENTATION DATA, THE WIRELESS POSITION AND ORIENTATION DATA ASSOCIATED WITH THE INERTIAL MEASUREMENT UNIT OF THE WIRELESS TRACKING DEVICE OPERABLY ATTACHED TO THE OBJECT — 1330

USING THE REFERENCE DATA, THE POSITION AND ORIENTATION DATA, AND THE REGISTRATION DATA IN THE SURGICAL NAVIGATION SYSTEM — 1340

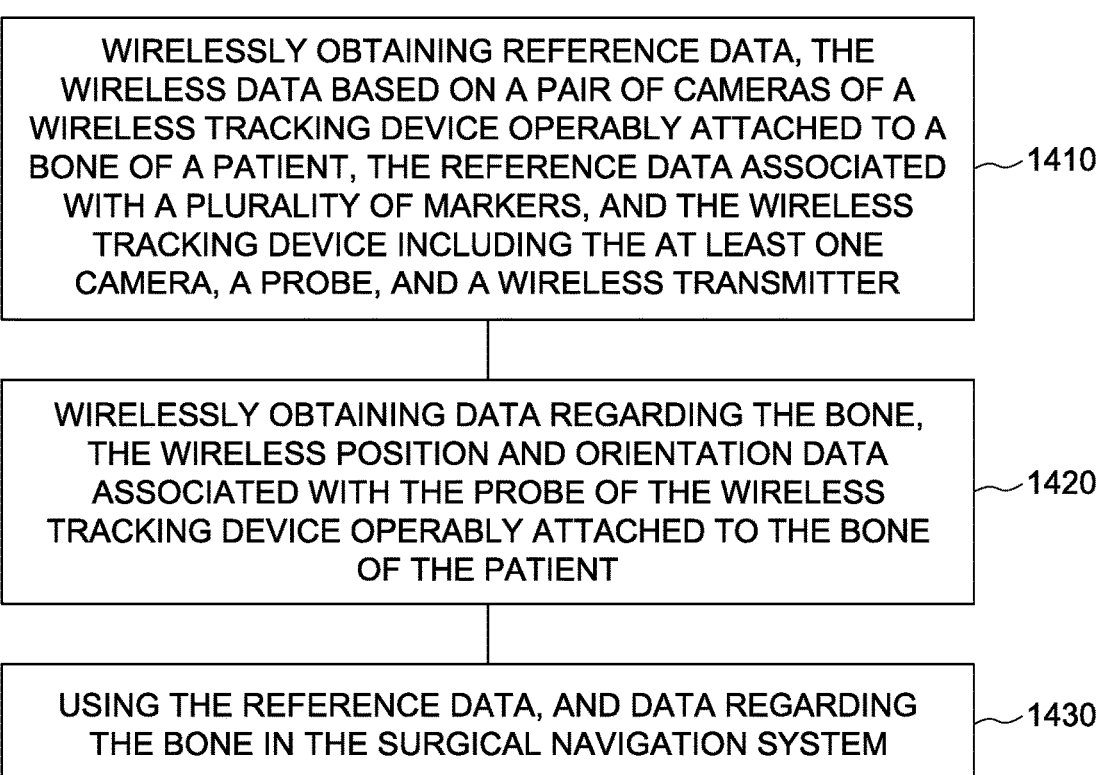

WIRELESSLY OBTAINING REFERENCE DATA, THE WIRELESS DATA BASED ON A PAIR OF CAMERAS OF A WIRELESS TRACKING DEVICE OPERABLY ATTACHED TO A BONE OF A PATIENT, THE REFERENCE DATA ASSOCIATED WITH A PLURALITY OF MARKERS, AND THE WIRELESS TRACKING DEVICE INCLUDING THE AT LEAST ONE CAMERA, A PROBE, AND A WIRELESS TRANSMITTER — 1410

WIRELESSLY OBTAINING DATA REGARDING THE BONE, THE WIRELESS POSITION AND ORIENTATION DATA ASSOCIATED WITH THE PROBE OF THE WIRELESS TRACKING DEVICE OPERABLY ATTACHED TO THE BONE OF THE PATIENT — 1420

USING THE REFERENCE DATA, AND DATA REGARDING THE BONE IN THE SURGICAL NAVIGATION SYSTEM — 1430

FIG. 18

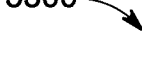
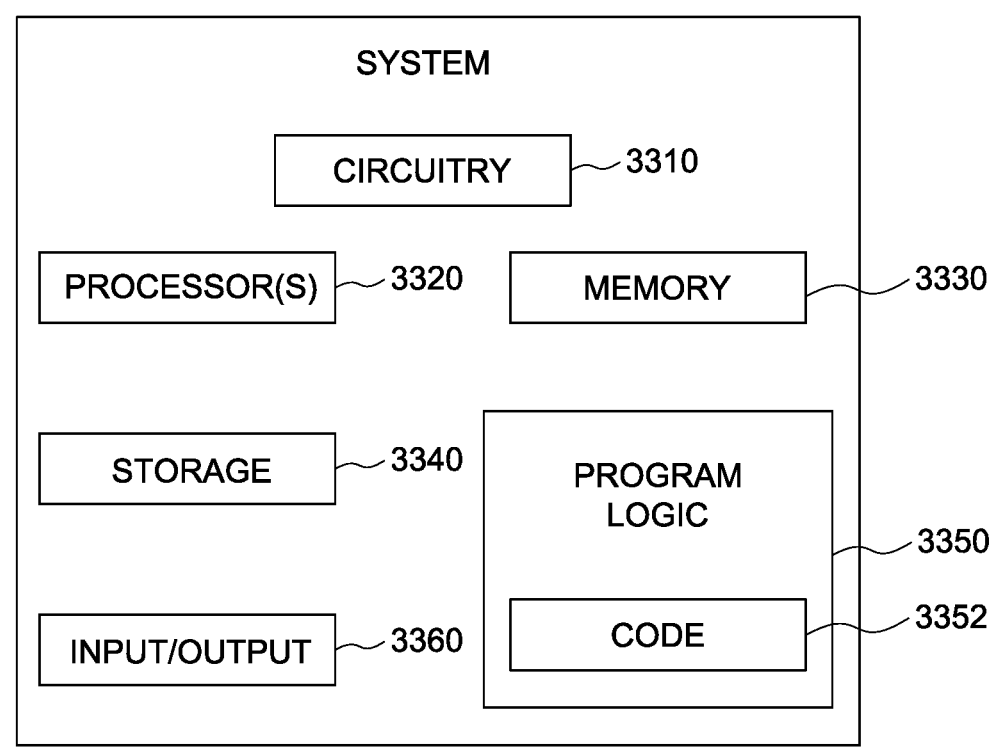
FIG. 21

4050

4051

Wireless transmitter

Bone

Ultrasound probe

4052

4050

4010

| T | C | B | | P | |

4014     4090     4070     4040     4012     4055     4016

NAVIGATIONAL AND/OR ROBOTIC TRACKING METHODS AND SYSTEMS

CROSS REFERENCE TO RELATED APPLICATION

This application is a by-pass continuation of PCT Application No. PCT/US2021/036985 filed on Jun. 11, 2021, which PCT application claimed priority from U.S. Provisional Patent Application No. 63/037,699, filed Jun. 11, 2020, entitled "Navigational And/Or Robotic Tracking Methods And Systems," which applications are hereby incorporated herein by reference in their entirety.

STATEMENT REGARDING FEDERAL FUNDING

This invention was made with government support under Award Number (FAIN) 2111012 awarded by the National Science Foundation. The government has certain rights in this invention.

FIELD OF THE DISCLOSURE

The present disclosure relates generally to surgical methods and systems, and more particularly to navigational and/or robotic tracking methods and systems employing inside-out tracking using one or more wireless tracking devices.

BACKGROUND

Typically, computer aided surgical applications require accurate tracking of objects of interest for performing a surgical procedure. One of the most common and widely used methods for surgical tracking is known as outside-in camera tracking. With reference to FIG. 1, an outside-in robotic tracking system 10 typically incudes stationary cameras 20 positioned in a fixed location away from the surgical field. The positions of the stationary cameras are generally inferred through methods of triangulation with fixed reference points.

The cameras 20 may be optical or infrared cameras and require a line of site to identifiable arrays that are rigidly fixed to the object of interest, for example, the patient's bone. Once the fixed camera position is known, the cameras can return the 3D position of the tracked object relative to the cameras and to a navigation application.

SUMMARY

Shortcomings of the prior art are overcome and additional advantages are provided through the provision, in one embodiment, of a surgical method, which includes for example, wirelessly obtaining reference data, the wireless data based on at least one camera of a wireless tracking device operably attached to a bone of a patient or to an object, the reference data associated with a plurality of markers, and the wireless tracking device including the at least one camera, and a wireless transmitter, and using the reference data in a surgical navigation system.

In another embodiment, a surgical method may include, for example, wirelessly obtaining reference data, the wireless data based on a plurality of cameras of a wireless tracking device operably attached to a bone of a patient or to an object, the reference data associated with a plurality of markers, and the wireless tracking device including the plurality of cameras, and a wireless transmitter, and using the reference data in a surgical navigation system.

In some embodiments, the camera position with respect to markers which may, by nonlimiting example, be attached to a robot and/or a tool attached to the robot, the base of a robot, a cart, a fixture attached to the surgical table, surgical lighting, or objects in the operating room.

In some embodiments, the returning the position and orientation data of the wireless tracking device to a surgical navigation application may be, for example, to update the target position for a surgical robot.

In some embodiments, the returning the position and orientation data of the wireless tracking device to a surgical navigation application may include the inertial measurement units returning changes in position from a starting position, and the camera used to register the starting position. Inertial measurement units may be subject to tracking drift over time. Regular reference measurements from the camera can correct tracking drift. The combination of the camera and the inertial measurement unit may increase accuracy and mitigates the risk of short-term occlusion. The camera may be operably to return position by referencing markers that are in known positions.

In some embodiments, the method of using the data may include, effecting a resection or excavation of the bone of the patient based on a cut plan and the position and orientation data of the wireless tracking device registered to the bone of the patient. In some embodiments, the camera of the wireless tracking device secured to the bone of the patient may reference a plurality of markers operably attached to the robot and/or a tool attached to the robot such as a custom tool or such as surfaces on an outside-in navigation camera.

In another embodiment, the camera of the wireless tracking device may be an infrared camera and the markers may be infrared emitters, for example, infrared LEDs.

In another embodiment, the camera of the wireless tracking device may be an infrared camera and the markers may be retroreflective fiducial markers.

In another embodiment, the camera of the wireless tracking device may be an optical camera and the markers may be a visual fiducial, for example, an AprilTag.

In another embodiment, the markers which are visible to the camera of the wireless tracking device may not be stationary, but attached to a moving surgical instrument, for example a robot, or tools attached to the robot, which may be non-stationary. The position of the components of the surgical instrument may be known, for example if the surgical instrument has intrinsic position data, for example joint encoders, or if the surgical instrument is tracked with a secondary camera. The position reference from the surgical instrument can be used to output the position of the marker so that the position of the marker is known when the camera of the wireless tracking device references the marker. If the real-time marker position is known, they need not be stationary to be used as reference points for the camera of the wireless tracking device.

In another embodiment, the imaging and tracking components of the wireless tracking device may be compact and light, weighing approximately 0.3 pounds and measuring 0.8 inches×0.7 inches×0.7 inches. In another embodiment, the camera of the imaging and tracking components of the wireless tracking device may provide a 240-degree field of view. In other embodiments, the wireless tracking device may be disposable, or may be reusable.

In another embodiment, the wireless tracking device may attach to a fixture that is rigidly attached to a bone. In another embodiment, the wireless tracking device may attach to surgical instruments such as retractors.

In another embodiment, the system may use a high number of markers (more than 3 markers) to aid in minimizing the risk of occlusion of the cameras and the markers. In other embodiments, the wireless tracking device may be positioned such that the camera is generally pointed towards the robot arm, or the wireless tracking device may be positioned such that the camera is generally pointed towards the robot base.

In another embodiment, a mounting plate may be rigidly attached to the bone. The position of the mounting plate relative to a bone origin may be known. The mounting plate may feature a locking locating mechanism, such as a dovetail, that is designed to interface with a locking feature of the wireless tracking device so that the wireless tracking device does not need to be registered to the bone, but is attached at a fixed known position.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 1 is a perspective view of a prior art outside-in robotic tracking system;

FIG. 14 is flowchart of a surgical process, according to an embodiment of the present disclosure;

FIG. 15 is a flowchart of a surgical process, according to an embodiment of the present disclosure;

FIG. 16 is flowchart of a surgical process, according to an embodiment of the present disclosure;

FIG. 17 is a flowchart of a surgical process, according to an embodiment of the present disclosure;

FIG. 18 is a flowchart of a surgical process, according to an embodiment of the present disclosure;

FIG. 21 is a block diagram of a system, according to an embodiment of the present disclosure;

DETAILED DESCRIPTION

Figure 2:
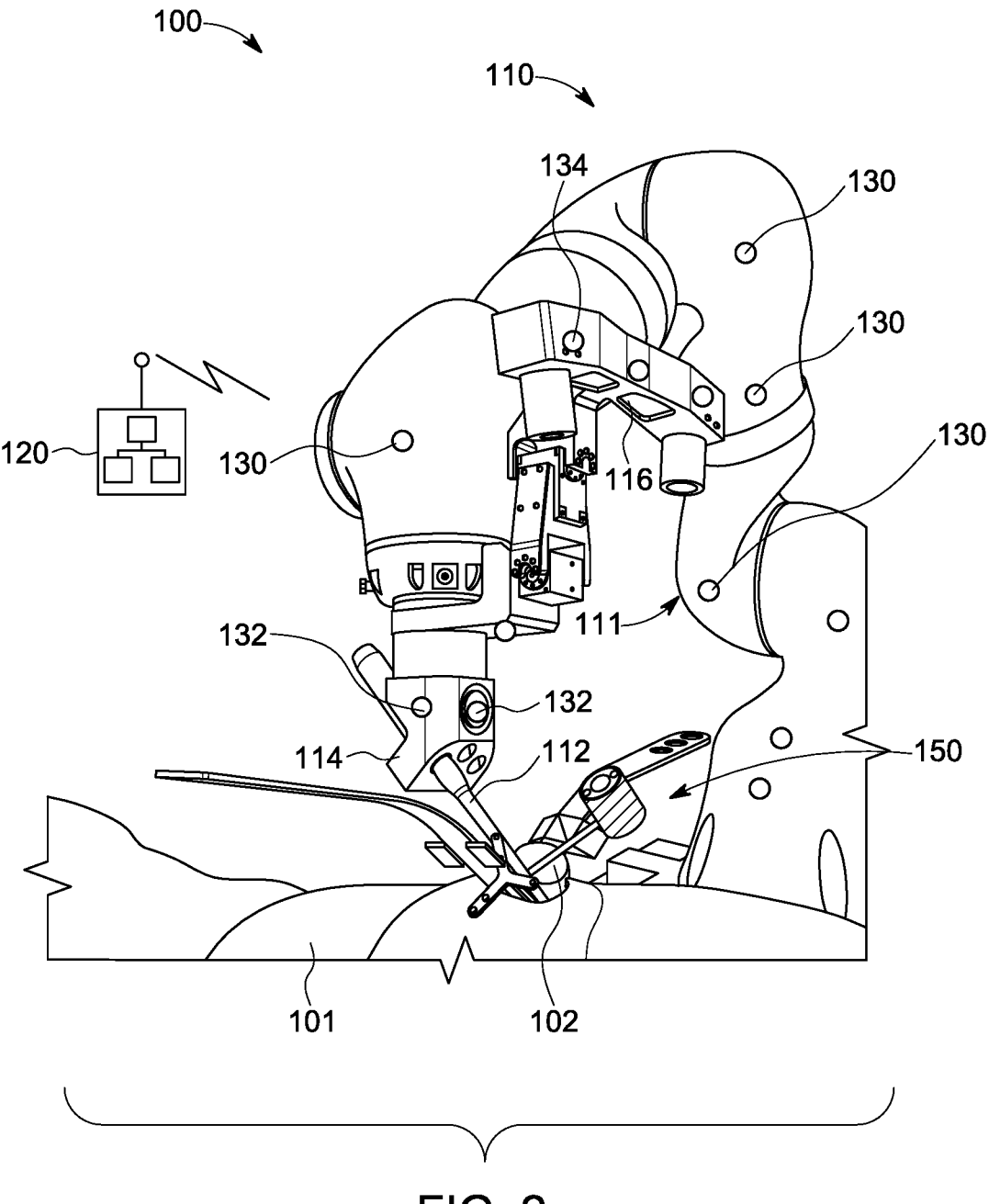
FIG. 2 is a perspective view of an inside-out robotic tracking system having a wireless tracking device attached to a bone of a patient and a plurality of markers attached to a robot, according to an embodiment of the present disclosure.

Generally stated, the present disclosure is directed to surgical methods and systems, and more particularly to and more particularly to navigational and/or robotic tracking methods and systems employing an inside-out tracking.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference.

Positions or directions may be used herein with reference to anatomical structures or surfaces. For example, as the current devices and methods are described herein with reference to use with the bones of the hip, the bones of the hip may be used to describe the surfaces, positions, directions or orientations of the implant apparatus, implant installation apparatus, and surgical methods. Further, the devices and surgical methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the tools and methods, and the aspects, components, features and the like thereof, described herein with respect to a right femur may be mirrored so that they likewise function with a left femur and vice versa.

In some embodiments, the technique of the present disclose may employ optical or infrared markers and wireless tracking devices attached to surgical objects such as a patient's bone or jig attached to the patient. The wireless tracking devices may be miniaturized devices having an integrated inertial measurement unit (IMU) and one or more camera sensors for attachment to surgical objects capable of returning orientation and distance relative to the markers. The technique may reduce or avoid and eliminate occlusion. The combination of an inertial measurement unit and a camera may allow for more accurate tracking of distance and orientation. The markers may be placed outside of the surgical field. In some embodiments, the markers may be active infrared markers such as infrared light emitting diodes (LEDs) and/or retroreflective fiducial markers. The active infrared markers or beacons may be place behind protective drapes outside the sterile field. In other embodiments, the wireless tracking device may include an optical camera and the markers may be a visual fiducial, for example, an AprilTag. The systems and methods may employ one marker, two markers or more than two markers. In some embodiments, the system and methods may use a high number of markers (more than 3 markers) to aid in minimizing the risk of occlusion of the cameras and the markers.

As will be appreciated from the present disclosure, rather than tracking the position of the object from stationary cameras like in the prior art, the object tracks its own position (similar to how human eyes determine the position of an individual). By combining a camera and an inertial measurement unit, both the position and orientation of the device, and thus, the object it is attached to can be accurately determined.

Generally, an initial position is captured by the camera and the position is updated by the inertial measurement unit with regular distance corrections by the camera. The object's position may be communicated wirelessly to a receiving device or controller for use with a robotic control application and/or with a navigation application.

FIG. 2 illustrates a robotic system 100 employing inside-out tracking for operably performing a surgical procedure on the patient 101 such as on a bone 102 of the patient 101, according to an embodiment of the present disclosure. For example, the robotic system 100 may generally include a robot 110 and a controller or computing unit 120 operably attached to the robot 110. The robot 110 may include a tool 112 attached to an end effector 114 of the robot 110. A plurality of markers 130 may be operably attached to the robot 110 such as the different portions of the arm 111 of the robot 110. A plurality of markers 132 may be operably attached to the end effector 114 of the robot 110. A plurality of markers 134 may be operably attached to a handle 116 of the robot 110. The markers may be active infrared beacons such as infrared light emitting diodes.

A wireless tracking device 150 may be operably attached to the bone 102 of the patient 101. The wireless tracking device 150 may be positioned such that it is generally pointing towards the robot 110 and base. Because of the proximity of the robot 110 and the wireless tracking device 150, the risk of occlusion may be reduced. The controller 120 may wirelessly communicate with the robot 110 and receive wireless signals or data from the wireless tracking device 150.

Figure 3:
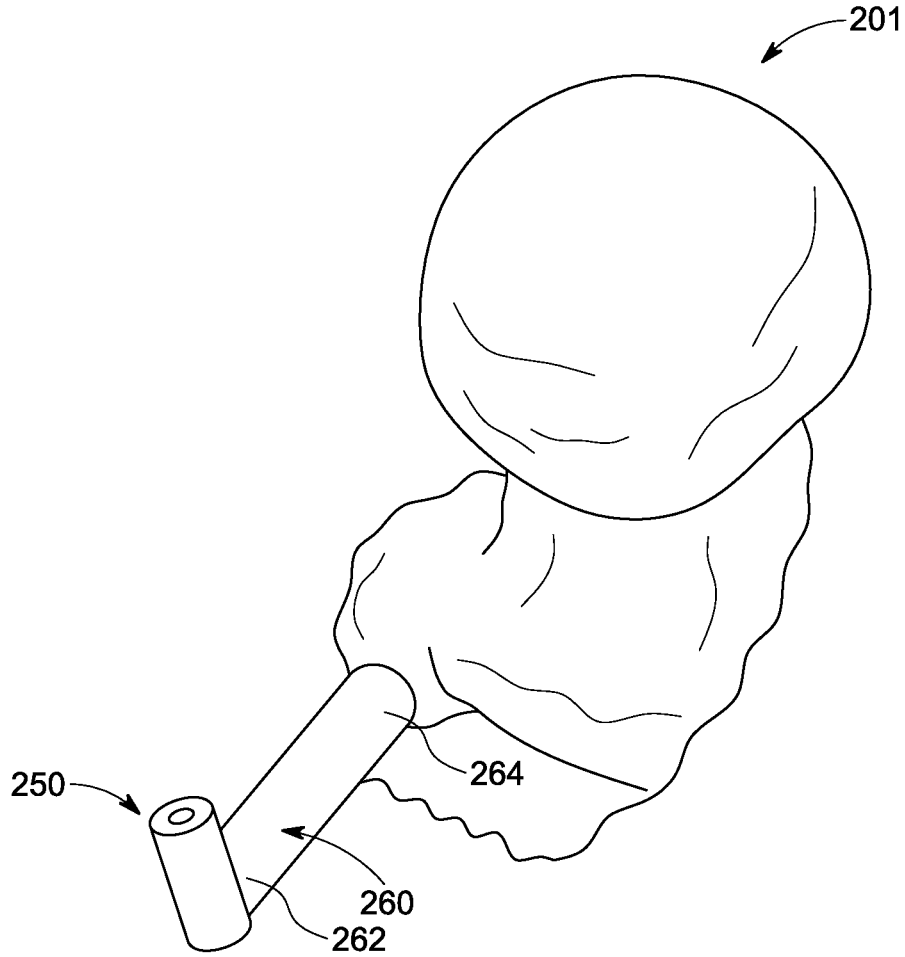
FIG. 3 is a perspective view of a wireless tracking device attached to a bone of a patient, according to an embodiment of the present disclosure.

As shown in FIG. 3, a wireless tracking device 250 may be attached to a first end of a support 260. A second end 264 of the support 260 may be attached to a bone 201 of a patient. For example, a surgeon may register the position and orientation of the wireless tracking device 250 to the patient's bone 201. In some embodiment, the robotic system 100 may be operable to register the wireless tracking device to the patient's bone.

Figure 4:
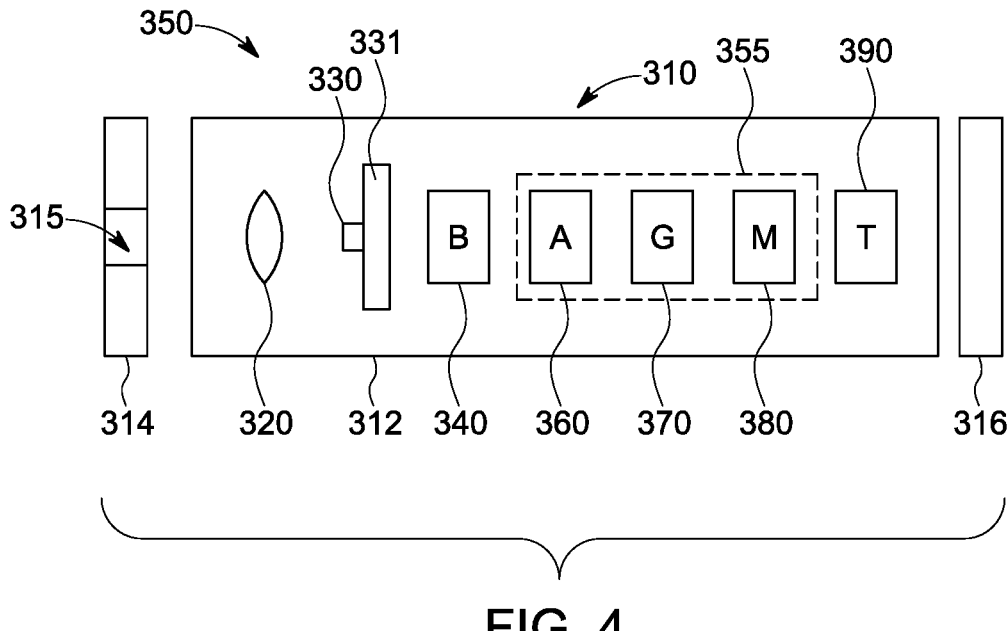
FIG. 4 is block diagram of a wireless tracking device, according to an embodiment of the present disclosure.

FIG. 4 illustrates a wireless tracking device 350, according to an embodiment of the present disclosure. In this illustrated embodiment, the wireless tracking device 350 may include a housing 310 having a hollow body 312, a first end cap 314 having an opening 315 therein, and a second end cap 316. Within the housing 310 may be a lens 320, a sensor 330 disposed on a circuit board 331, a power supply such as a battery 340, an inertial measurement unit 355, and a wireless transmitter 390. The inertial measurement unit 355 may be operable to determine orientation and linear acceleration, and may include an accelerometer 360, a gyroscope 370, and a magnetometer 380. In some embodiments, the inertial measurement unit 355 may include three (3) accelerometers, three (3) gyroscopes, and three (3) magnetometers, e.g., one per axis for each of the three axes of the wireless tracking device: roll, pitch, and yaw. The sensor 330 may be a charge-coupled device (CCD), complementary metal-oxide-semiconductor (CMOS) image sensor. In some embodiments, the sensor 330 may be a passive infrared sensor (PIR sensor) that measures infrared (IR) light radiating from objects in its field of view. In some embodiments, a plurality of lenses and sensors such as a pair of sensors, e.g., a pair of optical sensors or an optical sensor and an infrared sensor may be operably employed. The camera may have a wide field of view, for example, 240 degrees or other suitable field of view. The wireless tracking device 350 may be a miniaturized device having a 16 millimeter (mm) diameter body (or a height and width of 16 mm) and a length of 20 mm. In another embodiment, the imaging and tracking components of the wireless tracking device 350 may be compact and light, weighing approximately 0.3 pounds and measuring 0.8 inches×0.7 inches×0.7 inches. It will be appreciated that the wireless tracking device 350 may have other suitable configurations and sizes. The wireless tracking device 350 may be manufactured economically and may be disposable or reusable.

Figure 5:
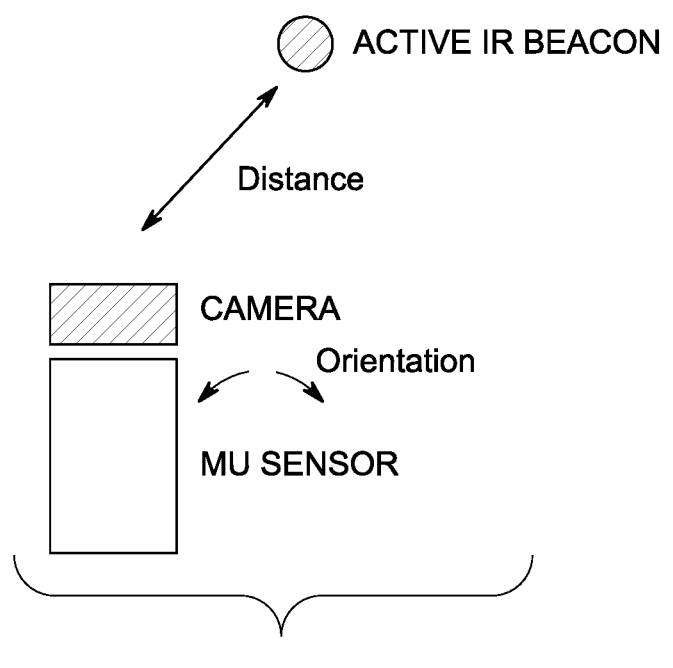
FIG. 5 is a block diagram of a wireless tracking device and a beacon, according to an embodiment of the present disclosure.

As shown in FIG. 5, the camera such as a lens and sensor may be operable to determine distance, and the inertial measurement unit may be operable to determine orientation.

Figure 6:
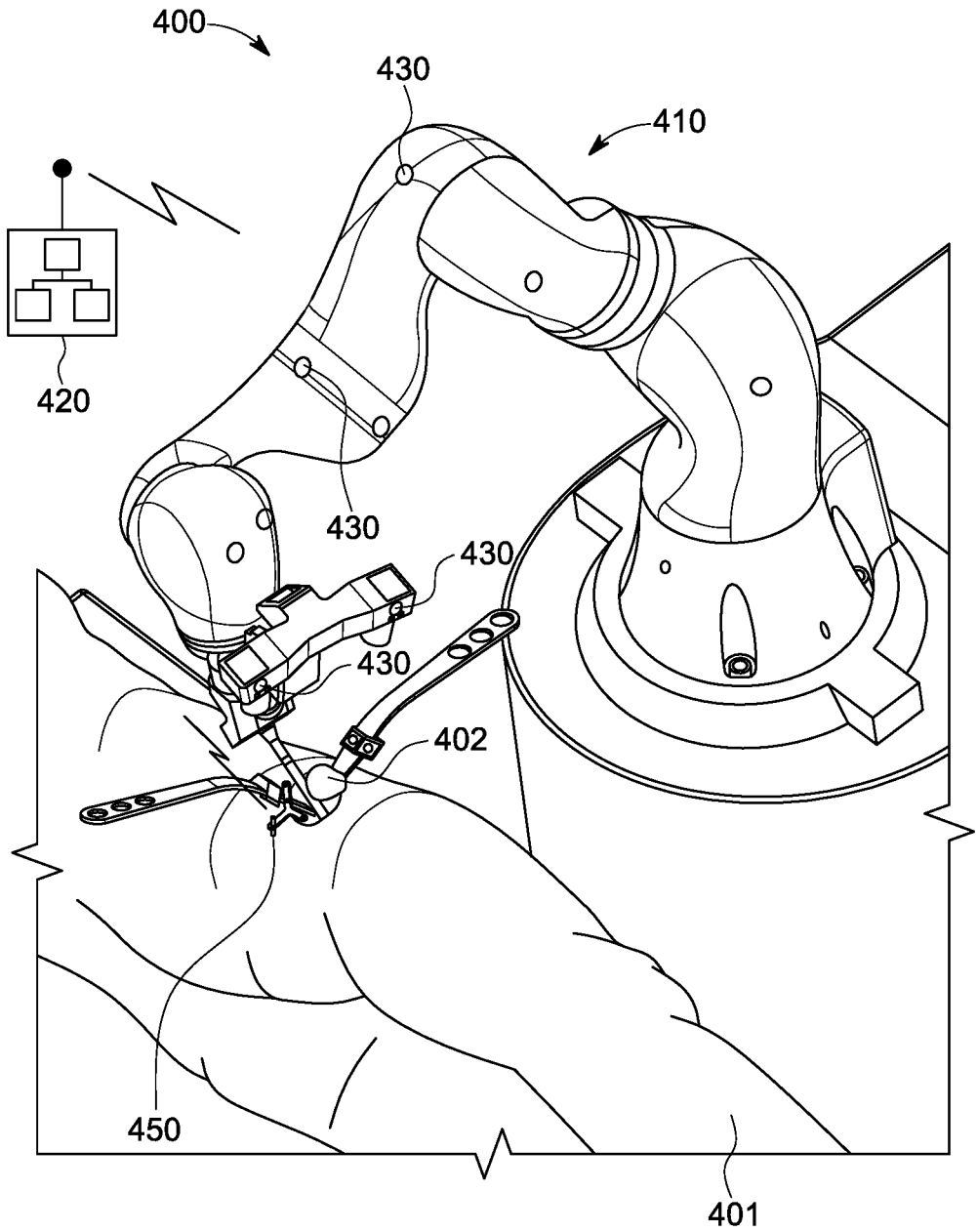
FIG. 6 is a perspective view of an inside-out robotic tracking system having a wireless tracking device attached to a bone of a patient and a plurality of markers attached to a robot, according to an embodiment of the present disclosure.

FIG. 6 illustrates a robotic system 400 employing inside-out tracking for operably performing a surgical procedure on the patient 401 such as on a bone 402 of the patient 401, according to an embodiment of the present disclosure. For example, the robotic system 400 may generally include a robot 410 and a controller or computing unit 420 operably attached to the robot 410. A plurality of markers 430 may be operably attached to the robot 410 such as the different portions of the arm of the robot 410, the end effector of the robot 410, and a handle of the robot 410. The markers may be active infrared beacons such as infrared light emitting diodes. The wireless tracking device 450 may be operably attached to the bone 402 of the patient 401. The controller 420 may wirelessly communicate with the robot 410 and receive wireless signals or data from the wireless tracking device 450.

Figure 7:
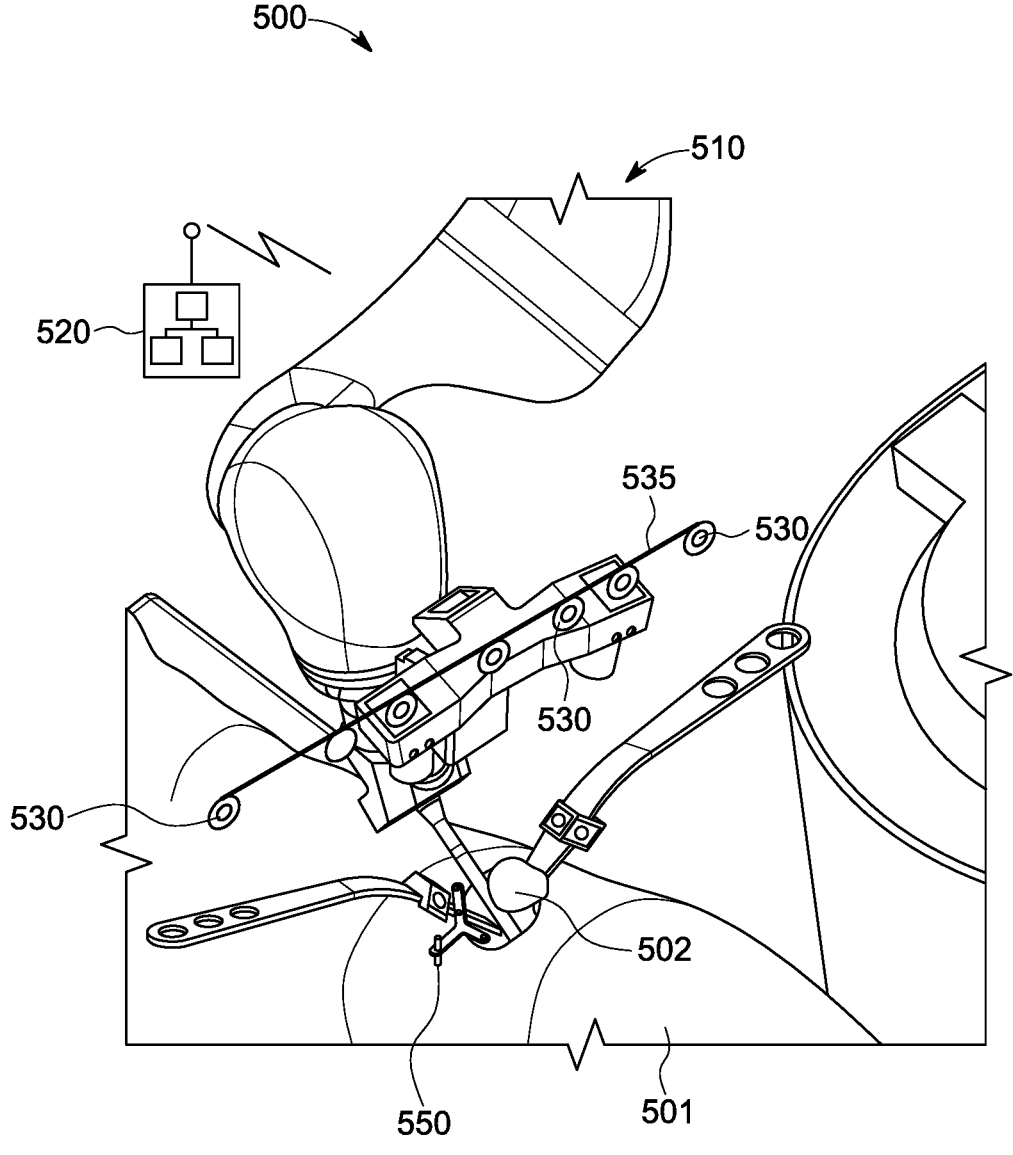
FIG. 7 is a perspective view of an inside-out robotic tracking system having a wireless tracking device and a plurality of markers attached to a robot, according to an embodiment of the present disclosure.

FIG. 7 illustrates a robotic system 500 employing inside-out tracking for operably performing a surgical procedure on the patient 501 such as on a bone 502 of the patient 501, according to an embodiment of the present disclosure. In this illustrated embodiment, a plurality of active infrared beacons 530 may be attached to a custom beacon array 535 that attaches to the robot 510 for increased visibility. The controller 520 may wirelessly communicate with the robot 510 and receive wireless signals or data from a wireless tracking device 550.

Figure 8:
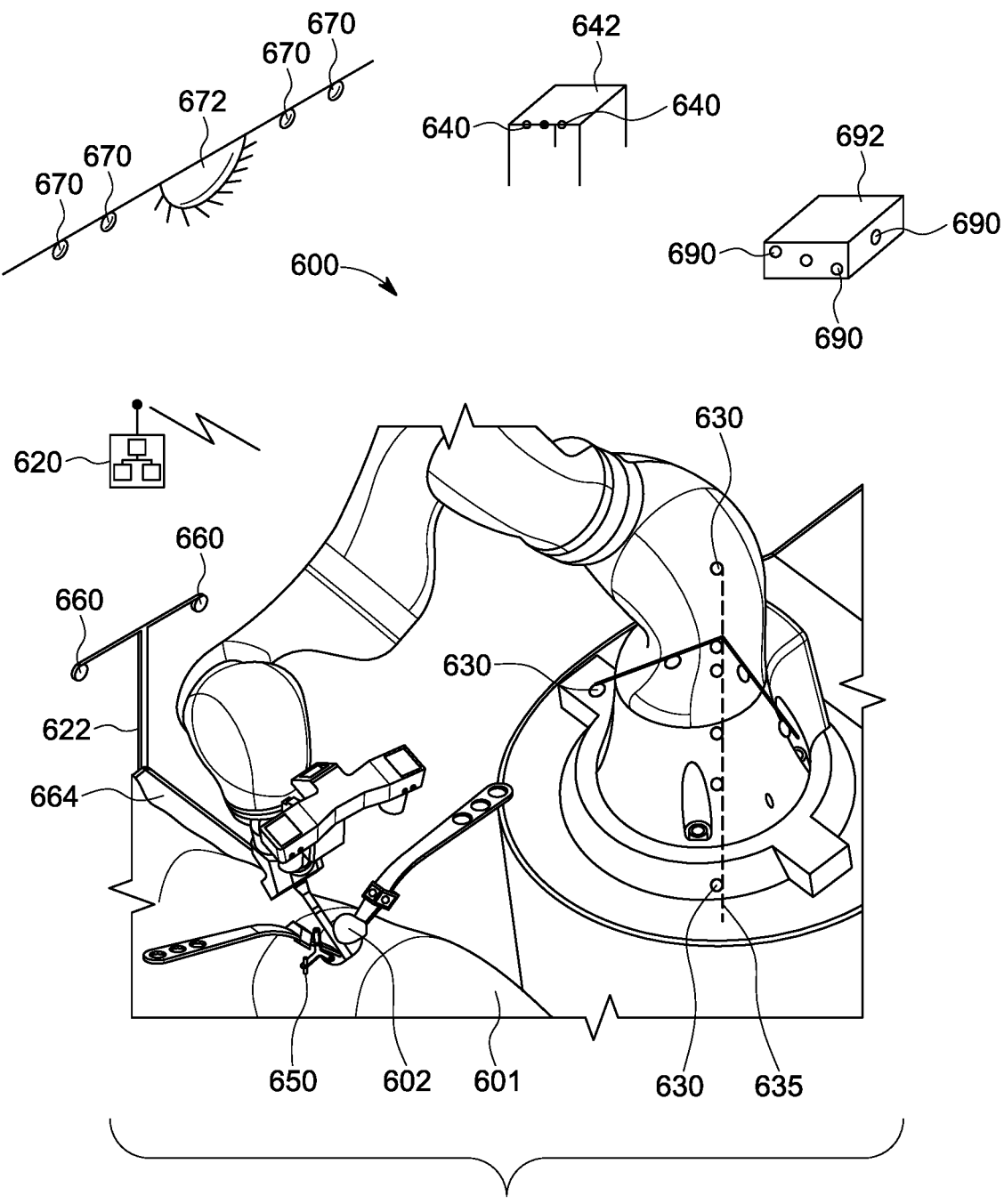
FIG. 8 is a perspective view of an inside-out robotic tracking system having a wireless tracking device attached to a bone of a patient and a plurality of markers attached to a robot, according to an embodiment of the present disclosure.

FIG. 8 illustrates a robotic system 600 employing inside-out tracking for operably performing a surgical procedure on the patient 601 such as on a bone 602 of the patient 601, according to an embodiment of the present disclosure. In this illustrated embodiment, a plurality of active infrared beacons 630 may be attached to a custom beacon array 635 that attaches to the base of the robot 610 for increased visibility. In other embodiments, a plurality of markers 640 may be attached to a cart 642, a plurality of markers 660 may be attached to a fixture 662 attached to a surgical table 664, a plurality of markers 670 may be attached to surgical lighting 672, a plurality of markers 690 may be attached to surfaces on an outside-in navigation camera 692, and/or a plurality of markers may be attached to other objects in an operating room. The controller 620 may wirelessly communicate with the robot 610 and receive wireless signals or data from a wireless tracking device 650.

Figure 9:
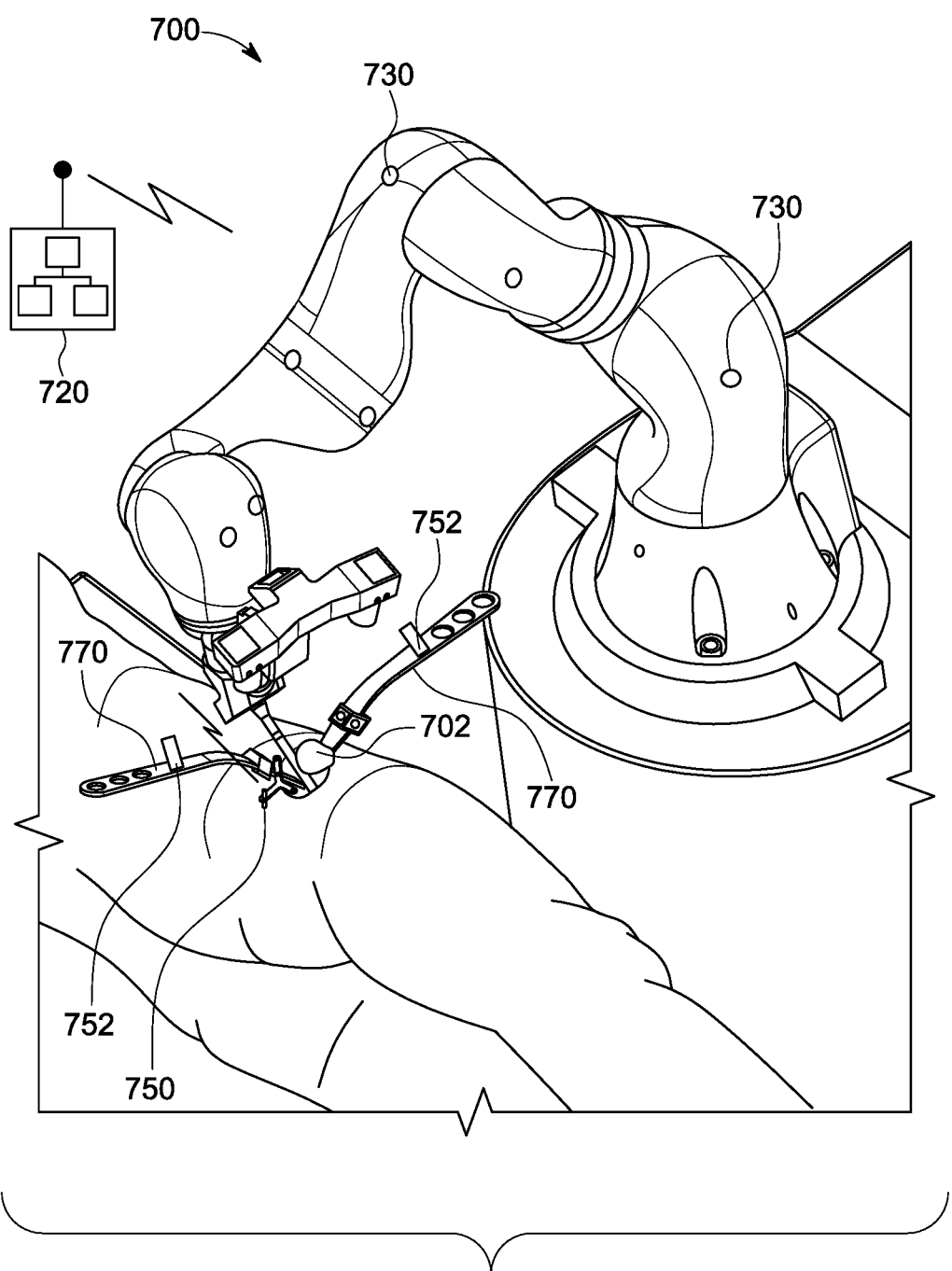
FIG. 9 is a perspective view of an inside-out robotic tracking system having a wireless tracking device attached to a bone of a patient, wireless tracking devices attached to a plurality of retractors, and a plurality of markers attached to a robot, according to an embodiment of the present disclosure.

FIG. 9 illustrates a robotic system 700 employing inside-out tracking for operably performing a surgical procedure on the patient 701 such as on a bone 702 of the patient 701, according to an embodiment of the present disclosure. In this illustrated embodiment, a wireless tracking device 750 may be attached to an object such as a retractor 770. The wireless tracking device 750 may also be attached to surgical objects such as retractors 770, to return the position of retractors 770. The advantage of the wireless tracking device 750 having a camera and an IMU sensor combined is that the camera can return the distance, which is known because the IR beacon position is known, and the IMU sensor can return the orientation.

Figure 10:
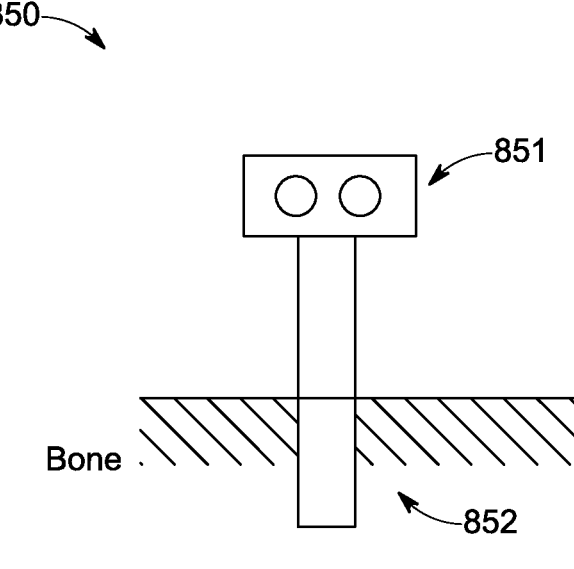
FIG. 10 is diagrammatic illustration of a wireless tracking device, according to an embodiment of the present disclosure.

FIG. 10 illustrates a wireless tracking device 850, according to an embodiment of the present disclosure. In this example embodiment, the wireless tracking device 850 may not include an inertial measurement unit. In addition, the wireless tracking device 850 may not include a plurality of cameras. For example, the wireless tracking device 850 may include at one end a camera portion 851 having a plurality of cameras such as a pair of cameras (binocular), and at a second end a sensor/probe portion 852. The sensor portion 852 may be disposable or insertable in a bone of a patient. Alternatively, the wireless tracking device 850 may be locked into a plate that is rigidly attached to the bone of the patient. The sensor probe 852 is operable to scan the interior surface or structure of the bone and return its position and orientation relative to the bone. From the position and orientation data, the position of the camera can be inferred, and thus, registered to the bone of the patient. In some embodiments, the wireless tracking device 850 may be enclosed in a case or housing so that it can be autoclaved without damaging the electronics.

Figure 11:
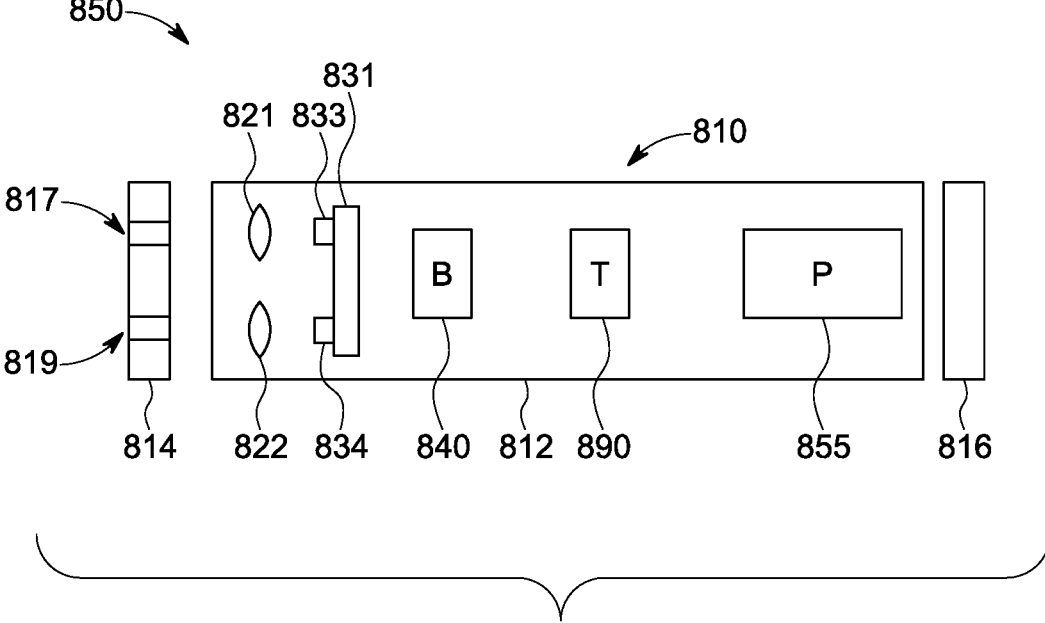
FIG. 11 is block diagram of the wireless tracking device of FIG. 10, according to an embodiment of the present disclosure.

As shown in FIG. 11, the wireless tracking device 850 may include a housing 810 having a hollow body 812, a first end cap 814 having a first opening 817 and a second opening 819 therein, and a second end cap 816. Within the housing 810 may be a first lens 821 and a second lens 822, a first sensor 833 and a second sensor 834 may be disposed on a circuit board 831, a power supply such as a battery 840, a probe 855, and a wireless transmitter 890. The probe 855 may be operable to determine interior surface or structure of the bone and may be an ultrasound probe. The sensors 833, 834 may be charge-coupled devices (CCD), complementary metal-oxide-semiconductor (CMOS) image sensors. In some embodiments, the sensors 833, 834 may be passive infrared sensors (PIR sensor) that measures infrared (IR) light radiating from objects in its field of view. Each of the cameras may have a wide field of view, for example, 240 degrees or other suitable field of view. The wireless tracking device 850 may be a miniaturized device having a 16 millimeter (mm) diameter body (or a height and width of 16 mm) and a length of 20 mm. In another embodiment, the components of the wireless tracking device 850 may be compact and light, weighing approximately 0.3 pounds and measuring 0.8 inches×0.7 inches×0.7 inches. It will be appreciated that the wireless tracking device 850 may have other suitable configurations and sizes. The wireless tracking device 850 may be manufactured economically and may be disposable or reusable.

In conventional tracking, objects such as fiducial array markers visible to stationary cameras are rigidly placed in patient bone. The position of these markers relative to the bone are commonly registered via various surface mapping techniques. The sampling of surface points can be time consuming and inefficient. A tracking system may be rigidly mounted to patient bone. An ultrasound probe, which may be inserted into a bone cavity and may be rigidly attachable to the tracking system construct, may be used to register the position of the tracking system. The ultrasound probe may be capable of transmitting and receiving data. The ultrasound probe is capable of detecting by way of non-limiting example, regions of relative bone density, for example between the less dense cancellous bone and the denser cortical bone. A shape such as a volume may be reconstructed by the ultrasound probe that visualizes the inner cortical wall relative to the ultrasound probe. Algorithmically the sampled shape or volume may be matched to the pre-operative data to infer the position of the probe relative to the bone. Because the probe is rigidly attached to the tracking system construct, it may be possible to infer the position of the tracking system relative to the bone, i.e. the position of the tracking system may be registered from the readings of the ultrasound probe.

In another embodiment the ultrasound probe may be inserted into a bone cavity and used to register the bone position. The probe may be movable within the bone. The probe may be tracked with a camera or the position of the probe may be inferred algorithmically at each position reading. The position of a fixed fiducial array may be inferred relative to position readings of the probe.

In another embodiment the ultrasound probe may be inserted into a bone cavity and used to generate pre-operative data for a surgical robotic system or surgical navigation system (also, computer aided surgical system). Many computer aided surgical systems rely on patient specific imaging to plan surgical procedures. This data may be generated from readings with an ultrasound probe inserted into a bone cavity.

In other embodiments, a wireless tracking device may include at least one camera or a plurality of cameras, a probe such as an ultrasound probe, and an inertial measurement unit such as described above.

It is noted that the infrared beacons may be stationary or mobile, as long as their position is known. For example, the markers which are visible to the camera of the wireless tracking device may not be stationary, but attached to a moving surgical instrument, for example a robot, or tools attached to the robot, which may be non-stationary. The position of components of the surgical instrument may be known, for example if the surgical instrument has intrinsic position data, for example joint encoders, or if the surgical instrument is tracked with a secondary camera. The position reference from the surgical instrument can be used to output the position of the marker so that the position of the marker is known when the camera of the wireless tracking device references the marker. If the real-time marker position is known, they need not be stationary to be used as reference points for the camera of the wireless tracking device.

For example, if the beacons are affixed to the robot, the position can be known through the control loop of the robot. It is also noted that the active beacons may be behind a sterile drape without material degradation of tracking performance. Active infrared beacons are capable of transmitting through plastics and low-density objects. The position of the tracked object is sent to the guidance application or control application wirelessly, for example with a 2.4 GHz radio signal.

As described below, in some embodiments, the robotic systems employing the wireless tracking device or devices may be operable for automatically effecting a cut plan. In other embodiments, a navigation system may employ one or more wireless tracking device or devices in which images may be displayed on a display for use by a surgeon while performing surgery. For example, the one or more wireless tracking device or devices may be operably attached to the patient for obtaining observation of the site for the surgical procedure.

Figure 12:
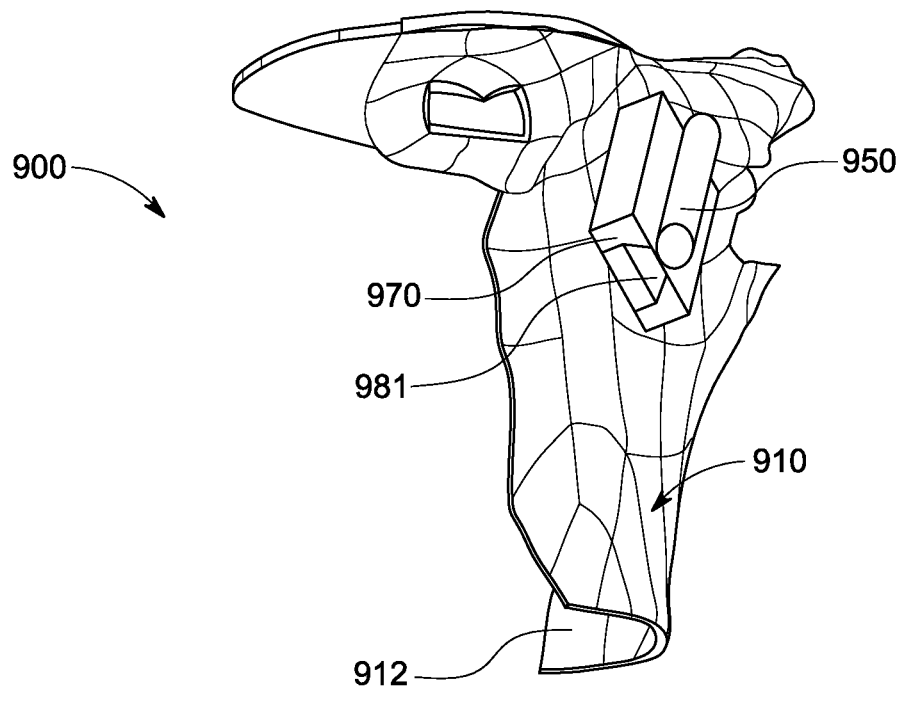
FIG. 12 is a first perspective view of a patient specific bone jig with a wireless tracking device, according to an embodiment of the present disclosure.

With reference to FIG. 12, therein illustrated is a mounting plate 900 that may be rigidly attached to a bone (not shown in FIG. 12), such as to a proximal portion of a tibia of a patient, according to an embodiment of the present disclosure. The position of the mounting plate relative to a bone origin may be known, e.g., the mounting plate may be a custom patient specific jig. The mounting plate or jig 900 may feature a locking locating mechanism 970, such as a female portion of a dovetail, which is positioned and registered to the mounting plate or patient specific bone jig 900. The locking locating mechanism 970 may be designed to interface with a locking feature, such as a male dovetail portion 981, which male dovetail portion 981 is operably attached to a wireless tracking device 950 so that the wireless tracking device 950 does not need to be registered directly to the patient's bone, but is attached at a fixed known position upon attachment and fixation of the mounting plate or jig 900 to the patient's bone.

Figure 13:
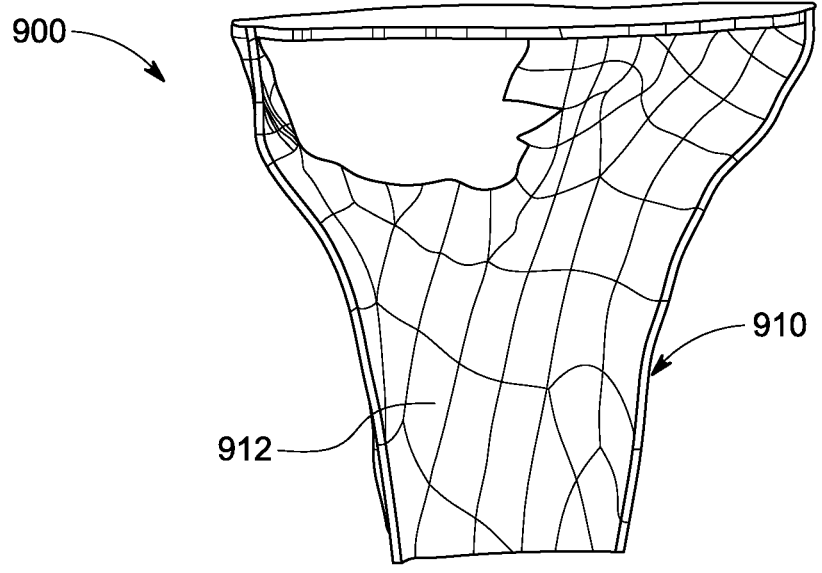
FIG. 13 is a second perspective view of the patient specific bone jig with the wireless tracking device of FIG. 10, according to an embodiment of the present disclosure.

As shown in FIGS. 12 and 13, the mounting plate or patient specific bone jig 900 may include a body 910. In this illustrated embodiment, the mounting plate or patient specific bone jig 900 may include an inner surface 912 contoured to match the outer surface portion of the patient's bone for proper placement and alignment and may be generated from a pre-operative image or data such as a suitable medical scan. Once a surgeon places the mounting plate or patient specific bone jig 900 on the proper bone surface location, and the wireless tracking device is registered to patient's bone.

FIG. 14 illustrates a surgical method 1000, according to an embodiment of the present disclosure. In this illustrated embodiment, the surgical method 1000 includes at 1100, wirelessly obtaining reference data, the wireless data based on at least one camera of a wireless tracking device operably attached to the bone of the patient, the reference data is associated with a plurality of markers, and the wireless tracking device including at least one camera, and a wireless transmitter, at 1200 using the reference data in a surgical navigation system.

FIG. 15 illustrates a surgical method 1100, according to an embodiment of the present disclosure. In this illustrated embodiment, the surgical method 1100 includes at 1110, wirelessly obtaining reference data, the wireless reference data is based on at least one camera of a wireless tracking device operably attached to the bone of the patient, the reference data is associated with a plurality of markers, and the wireless tracking device including at least one camera, and a wireless transmitter, at 1120 generating data regarding registration of the wireless tracking device relative to the bone of the patient, and at 1130 using the reference data and the data regarding registration of the wireless tracking device to the bone of the patient and the obtained reference data in the surgical navigation system.

FIG. 16 illustrates a surgical method 1200, according to an embodiment of the present disclosure. In this illustrated embodiment, the surgical method 1200 includes at 1210, wirelessly obtaining reference data, the wireless reference data based on at least one camera of a wireless tracking device operably attached to the bone of the patient, the reference data associated with a plurality of markers, and the wireless tracking device including the at least one camera, an inertial measurement unit, and a wireless transmitter, at 1220 generating data regarding registration of the wireless tracking device relative to the bone of the patient, at 1230 wirelessly obtaining position and orientation data, the wireless position and orientation data associated with the inertial measurement unit of the wireless tracking device operably attached to the bone of the patient, and at 1240 using the reference data, the position and orientation data, and the registration data in the surgical navigation system.

FIG. 17 illustrates a surgical method 1300, according to an embodiment of the present disclosure. In this illustrated embodiment, the surgical method 1300 includes at 1310, wirelessly obtaining reference data, the wireless reference data based on at least one camera of a wireless tracking device operably attached to an object, the reference data associated with a plurality of markers, and the wireless tracking device including the at least one camera, an inertial measurement unit, and a wireless transmitter, at 1320 obtaining or generating data regarding registration of the wireless tracking device relative to the object, at 1330 wirelessly obtaining position and orientation data, the wireless position and orientation data associated with the inertial measurement unit of the wireless tracking device operably attached to the object, at 1340 using the reference data, the position and orientation data, and the registration data in the surgical navigation system.

FIG. 18 illustrates a surgical method 1400, according to an embodiment of the present disclosure. In this illustrated embodiment, the surgical method 1400 includes at 1410, wirelessly obtaining reference data, the wireless reference data based on a pair of cameras of a wireless tracking device operably attached to the bone of the patient, the reference data associated with a plurality of markers, and the wireless tracking device including the at least one camera, a probe, and a wireless transmitter, at 1420 wirelessly obtaining data regarding the bone, the wireless position and orientation data associated with the probe of the wireless tracking device operably attached to the bone of the patient, and at 1430 using the reference data, and data regarding the bone in the surgical navigation system.

In the various disclosed embodiments, the returning the position and orientation data of the wireless tracking device to a surgical navigation application may be, for example, to update the target position for a surgical robot. In some embodiments, the returning the position and orientation data of the wireless tracking device to a surgical navigation application may include the inertial measurement units returning changes in position from a starting position, and the camera used to register the starting position. Inertial measurement units may be subject to tracking drift over time. Regular reference measurements from the camera can correct tracking drift. The combination of the camera and the inertial measurement unit may increase accuracy and mitigates the risk of short-term occlusion. The camera may be operable to return position by referencing the markers that are in known positions.

In some embodiments, the method of using the data may include effecting a resection or excavation of the bone of the patient based on a cut plan and the position and orientation data of the wireless tracking device registered to the bone of the patient. In some embodiments, the camera of the wireless tracking device secured to the bone of the patient may reference a plurality of markers operably attached to the robot and/or a tool attached to the robot such as a custom tool or such as surfaces on an outside-in navigation camera.

Figure 19:
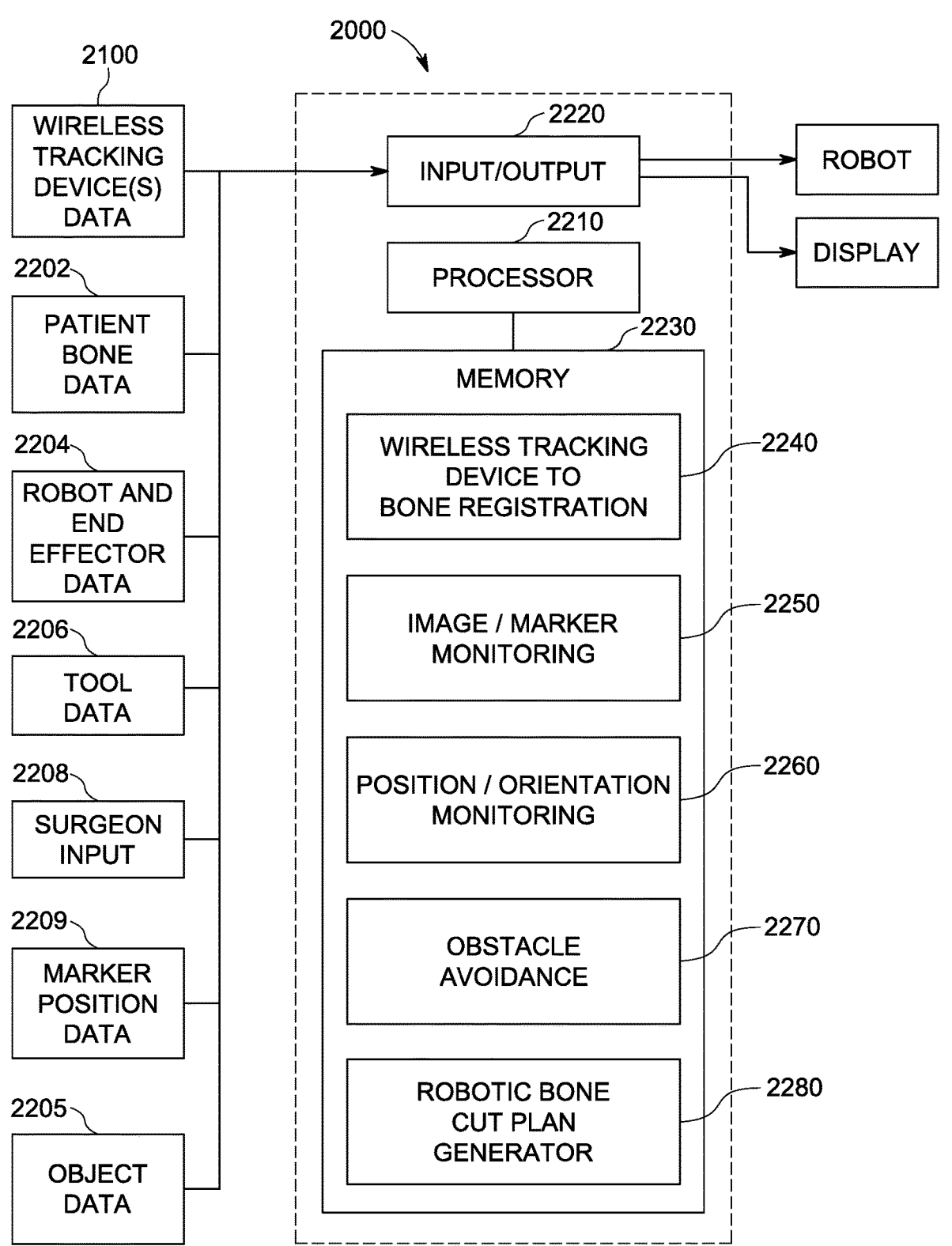
FIG. 19 is a block diagram of an inside-out robotic tracking system, according to an embodiment of the present disclosure.

FIG. 19 illustrates a block diagram of a system 2000 for implementing, for example, the surgical method 1000 (FIG. 14), the surgical method 1100 (FIG. 15), the surgical method 1200 (FIG. 16), the surgical method 1300 (FIG. 17), and the surgical method 1400 (FIG. 18), according to an embodiment of the present disclosure. The system 2000 may generally include a processing unit or processor 2210, input/output devices 2220, and memory 2230.

For example, wireless tracking device data 2100 may be obtained from the one or more wireless tracking devices such as image data may be obtained from a camera or an imager, infrared sensor, and position and orientation data from the inertial measurement system.

Patient bone data 2202, such as three-dimensional data representing at least a portion of a patient's bone such as the proximal portion of a femur of the patient may be obtained or inputted to the system 2000. The patient bone data 2202 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three-dimensional imaging or processing. Such data may be provided directly from an imaging machine or retrievable from a database of stored medical image data.

Robotic end effector data 2204, such as three-dimensional data or a model representing a robotic end effector, may be obtained or inputted to the system 2200. The robotic end effector data 2204 may include three-dimensional data previously generated, for example, based on scanning of the robotic end effector or based on CAD models.

Tool data 2206, such as three-dimensional data or a model representing at least a portion of a robotic tool, (e.g., a working end such as a cutting end), may be obtained or inputted to the system 2000. The tool data 2206 may include three-dimensional data previously generated, for example, based on the scanning of the tool or data for fabricating the tool. For example, the tool data 2206 may be limited to sufficient data representing portions of the patient specific bone jig allowing for use in the robotic cut plan.

Further input data may include surgeon input 2208 such as desired general data regarding location, orientation, tool, patient specific bone jig, or other data.

The processor 2210 may be a computer operating system, for example, WINDOWS, OSX, UNIX or Linux operating system. In some embodiments, the processor 2210 may be a portable or handheld computing device. In other embodiments, the processing unit 2210 may be one or more operably connected processing units, computing devices, servers, linked or operating over one or more networks such as a global communications network, e.g., the Internet.

The memory 2230 may include various modules for processing the input data. For example, the memory 2230 may include a wireless tracking device to bone registration generator 2240, an image/marker monitoring 2250, position/orientation monitoring 2260, obstacle avoidance 2270, and a robotic bone cut plan generator 2280.

The wireless tracking device to bone registration generator 2240 may be operable to receive the patient bone data 2202, the wireless tracking device data 2100, and a surgeon input 2208 to determine the actual location and orientation of the patient's bone such as when the patient is disposed on an operating table. For example, using the patient bone data or bone model, suitable programing may be provided for locating and orienting the actual patient's bone based on the wireless tracking device data and the observed actual patient specific bone.

The robotic bone cut plan generator 2280 may be operable to determine data or instructions for operating a surgical robot or other automated devices for resecting the patient's bone. In some embodiments, a 3D model of the resected bone, such as a resected proximal portion of the patient's femur or tibia may be uploaded to the surgical robot to allow the surgical robot to be operable to effect a bone cut plan to resize the proximal portion of the femur or tibia autonomously, or semi-autonomously to form, for example, a resection and/or form one or more cavities in the bone. The data or instructions may be combined with data received from the wireless tracking devices. A suitable surgical robot may be an LBR iiwa Kuka robot manufactured by KUKA ROBOTICS Corporation of Shelby Township, Michigan, and may be operable with one or more bone saws, rasps, saws, drills, and/or other devices. The robotic bone cut plan generator 2280 may include various modules such as a resection surface or surface generator, a cavity or cavities generator, and an optimizing generator. The robotic bone cut plan generator 2280 may allow for a surgeon to indicate, for example, a resection plane or such plane may be automatically generated provided, e.g., by input from a surgeon, or based on or utilizing predetermined data. The robotic bone cut plan generator 2280 may include receiving initial inputs from a surgeon such as locations, widths, lengths, depths, or may be based on or utilizing predetermined data.

Figure 20:
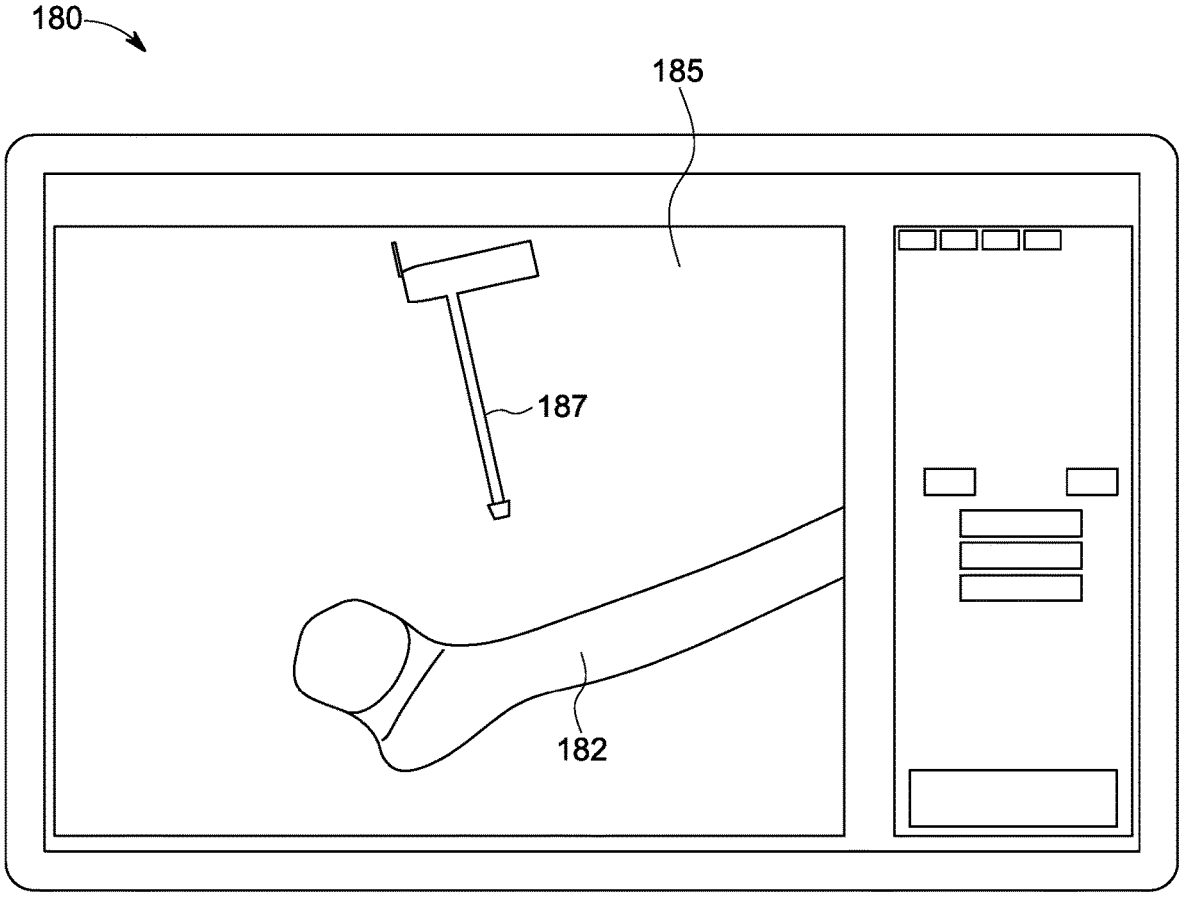
FIG. 20 is a view of a display illustrating a bone and a tool, according to an embodiment of the present disclosure.

FIG. 20 illustrates a display or monitor 180, according to an embodiment of the present disclosure. For example, a wireless tracking device may be operably attached to a bone of a patient, as described above. The inertial measurement unit may provide position and orientation data regarding the registered wireless tracking device may be used, for example, in combination with three-dimensional bone data (e.g., block 2202, FIG. 19) to generate a representation of the bone 182 or portion of the bone 182 of the patent on a display or monitor 180. In addition, the camera of the wireless tracking device may provide image data regarding the tool and used, for example, in combination with three-dimensional tool data (e.g., block 2206, FIG. 19) to generate a representation of the tool 187 or portion of the tool 187 of the patent on a display or monitor 180. Desirably, the relative position and orientation of the bone and tool may correspond to the actual position and orientation of the bone and tool. In some embodiments, the tool may be controlled by a robot, and in other embodiments, the tool may be manually controlled by a surgeon. In some embodiments, additional information may be displayed on the display or monitor 180. For example, retractors or other objects employed in the surgical procedure may include wireless tracking devices to allow representation of the object such as one or more retractors (and using three-dimensional data (e.g., block 2205, FIG. 19) to be also illustrated on the display 180 along with the representations of the bone 182 and the tool 187.

From the present disclosure, it will be appreciated that the present inside-out technique may overcome disadvantages compared to outside-in tracking.

For example, the present inside-out technique may reduce the likelihood of occlusion issues compared to outside-in systems where the cameras must maintain line of site to the identifiable arrays at all times and can limit the number of assistants that can help the surgeon and can constrain the freedom to operate.

In outside-in systems require registration of the cameras in space. The camera position(s) need(s) to be precisely known. Generally, the cameras need to be registered to a fixed position and generally need to maintain line-of-site to the fixed position. For example, the cameras may be registered to the robot base through arrays that are mounted to the robot base. These arrays generally cannot be placed outside of the sterile field to maintain visibility to the cameras and require re-sterilization. The accuracy of the system tracking can be reduced by poor registration of the cameras to the known position. This process also introduces time to the surgical procedure. The technique of the present disclosure may allow registration wherein the wireless tracking devices need not be fixed in space.

In outside-in systems, the cost of the camera is high because the cameras are further away requiring very high resolution and capable of very high-speed processing. For example, NDI Vega XT cameras are known to be between $10,000 and $20,000 per camera. The technique of the present disclosure may employ wireless tracking devices having cameras that need not be high resolution.

The technique of the present disclosure may provide greater accuracy. The distance of the cameras to the tracked objects affects the tracking accuracy. Generally, the further the tracked objects from the tracking cameras the worse the tracking accuracy. In outside-in systems, because the cameras are outside of the sterile field, they have to be positioned at a distance that adversely affects tracking accuracy.

Outside-in systems also have a limited field of view, because the outside-in cameras are generally registered to a fixed position and cannot move.

The present inside-out tracking technique may eliminate the cost of expensive cameras or complex registrations. By introducing multiple active infrared beacons with a large field of view camera at known locations, the occlusion risks may be mitigated.

FIG. 21 illustrates a block diagram of another system 3300 for use in registration and/or tracking of a patient's bone employing a patient specific bone jig, which is part of the technical architecture of the embodiments of the present disclosure. System 3300 may include a circuitry 3310 that may in certain embodiments include a microprocessor 3320. The system 3300 may also include a memory 3330 (e.g., a volatile memory device), and storage 3340. The system 3300 may include a program logic 3350 including code 3352 that may be loaded into or stored in the memory 3330, the storage 3340, and/or circuitry 3310, and executed by the microprocessor 3320 and/or circuitry 3310. The various components may be operably coupled directly or indirectly via a system bus or may be coupled directly or indirectly to other data processing systems and components. The program logic 3350 may include the program code discussed above in this disclosure for use in forming a patient specific femoral stem of a femoral component for total hip replacement.

As will be appreciated by one skilled in the art, aspects of the technique may be embodied as a system, method, or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system".

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. Each block in the flowchart or block diagrams may represent a module, segment, or portion of code, which includes one or more executable instructions for implementing the specified logical function (s).

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. For example, in a particular arrangement, a desktop or workstation computer may be employed using a commercially available operating system, e.g. Windows®, OSX®, UNIX or Linux based implementation.

As shown in FIG. 21, the computer readable storage medium 3340 may be, for example, but not limited to, an electronic, magnetic, optical, electromagnetic, infrared or semiconductor system, apparatus, or device, or any suitable combination of the foregoing. The storage 3340 may include an internal storage device, an attached storage device and/or a network accessible storage device. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program code for carrying out operations for aspects of the present technique may be written in any combination of one or more programming languages, including an object oriented programming language, such as Java, Smalltalk, C++ or the like, and conventional procedural programming languages, such as the "C" programming language, PHP, ASP, assembler or similar programming languages, as well as functional programming languages and languages for technical computing. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

As shown in FIG. 21, Input/Output or I/O devices 3360 (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Data relating to a patient, e.g., the patient's pelvis and hip, may be created by, or accessed from, a medical sensor device. For example, previous medical scans of an extremity, such as those obtained from a computerized axial tomography (CAT or CT) or magnetic resonance imaging (MRI) scan may be stored in a medical record storage apparatus, in storage 3340, or accessed by system 3300. Such patient data may include other data for a given patient (e.g. bone density, type, length, medical conditions etc.). By way of a non-limiting example, the patient data may include a scan data set containing a series of two-dimensional images obtained from the scanning device (e.g. CT scan slices). As such, the scan data set is a 3D dimensional representation of the scan data.

It will be appreciated that the technique of the present disclosure may overcome the time and processing constraints of current state-of-the-art registration and tracking which employs manually sample a large number of points of interest. In particular, the technique of the present disclosure may overcome the disadvantage of the current registration methods include the need time required to manually sample a large number of points to achieve a high accuracy registration and the need for the registration to be performed by a skilled user.

For example, with the use of a camera, the present technique allows for thousands of points to be "sampled" in a very short time, increasing registration accuracy and reducing time. The registration can also be performed by a less skilled user.

From the present description, it will be appreciated that the technique of the present disclosure may provide methods for optimizing the scene, field of view, and a target to enhance the utility of depth cameras in the surgical field. To utilize a wireless tracking device for imaging, registration, and tracking in the surgical field, the camera of the wireless tracking device may be operable to 1) identify the clinically relevant object to track and, 2) the inertial measurement unit of the wireless tracking device may be operable to determine the pose or spatial position and orientation of the object.

In some embodiments the controller for an instrument configured to excavate bone may receive inputs from multiple navigation systems. In one embodiment there is an outside-in navigation system that is configured to track the position of the excavating instrument as well as the position of the bone (such as a robot via a tracking device affixed for example near the end of the robot and tracking devices affixed to the bone). In the same embodiment, there may be one or more inside-out sensors that may be configured to track surgical tools such as retractors. The tracked position of the retractors returned from the inside-out navigation system may be configured to guide the movement of the instrument. The controller is configured to take inputs for the bone and instrument position returned from the outside-in navigation system as well as inputs from the surgical tool positions to guide the movement of the instrument configured to excavate bone.

In some embodiments, the controller for an instrument configured to excavate bone may receive position data from multiple inside-out sensors. A dedicated inside-out sensor may track the position of the instrument configured to excavate bone, or a single dedicated sensor may track both the position of the instrument configured to excavate bone as well as the position of the bone. Inside-out trackers may also simultaneously track the relative position of surgical tools such as retractors. The tracked positions of the instrument configured to excavate bone, the bone position, and the positions of the tracked surgical tools can be combined to guide the movement of the robot.

In one embodiment, trackers may be added to surgical tools such as retractors. The inside-out tracker configured with a camera, an IMU, and a wireless transmitter may be attached to the bone. The camera is configured to have line of site to the trackers on the surgical tools and can return its position relative to the surgical tools. The position of the bone relative to the surgical tools may be used as one of several control inputs to guide an instrument configured to excavate bone.

In some embodiments, the inside-out tracker is not configured to be wireless but may be wired. The inside out track may be configured with a camera, an IMU and a cable for data transfer.

Figure 22:
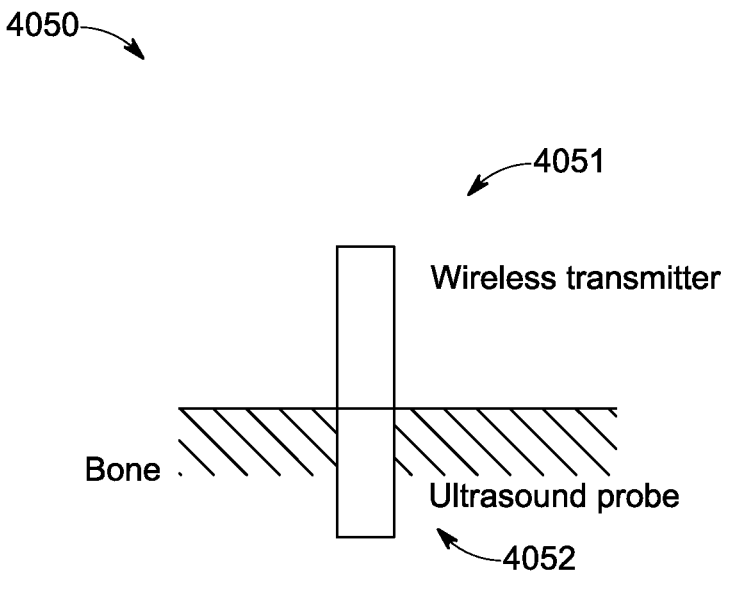
FIG. 22 is diagrammatic illustration of a wireless tracking device, according to an embodiment of the present disclosure.

FIG. 22 illustrates another a wireless tracking device 4000, according to an embodiment of the present disclosure. In this example embodiment, the wireless tracking device 4050 may not include one or more cameras or an inertial measurement unit. For example, the wireless tracking device 4050 may include at one end a wireless transmitter portion 4051, and at a second end a sensor/probe portion 4052. The sensor portion 4052 may be disposable or insertable in a bone of a patient. Alternatively, the wireless tracking device 4050 may be locked into a plate that is rigidly attached to the bone of the patient. The sensor probe 4052 is operable to scan the interior surface or structure of the bone and return its position and orientation relative to the bone. In some embodiments, the wireless tracking device 4050 may be enclosed in a case or housing so that it can be autoclaved without damaging the electronics.

Figure 23:
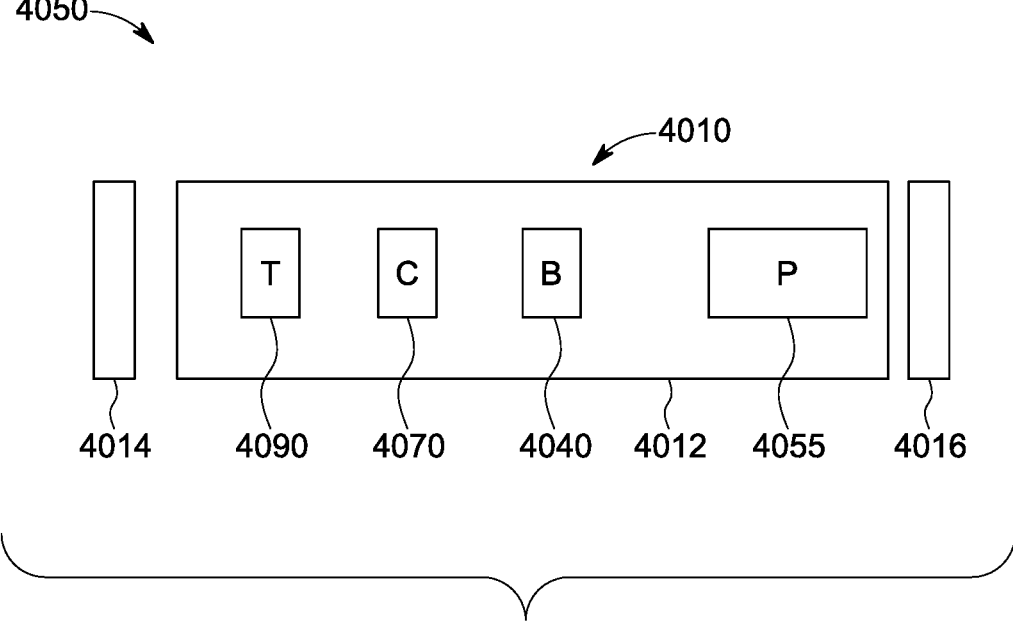
FIG. 23 is block diagram of the wireless tracking device of FIG. 22, according to an embodiment of the present disclosure.

As shown in FIG. 23, the wireless tracking device 4050 may include a housing 4010 having a hollow body 4012, a first end cap 4014, and a second end cap 4016. Within the housing 4010 may be a power supply such as a battery 4040, a processor 4070, a probe 4055, and a wireless transmitter 4090. The probe 4055 may be operable to determine interior surface or structure of the bone and may be an ultrasound probe. The wireless tracking device 4050 may be a miniaturized device having a 16 millimeter (mm) diameter body (or a height and width of 16 mm) and a length of 20 mm. In another embodiment, the components of the wireless tracking device 850 may be compact and light, weighing approximately 0.3 pounds and measuring 0.8 inches×0.7 inches×0.7 inches. It will be appreciated that the wireless tracking device 4050 may have other suitable configurations and sizes. The wireless tracking device 4050 may be manufactured economically and may be disposable or reusable.

An ultrasound probe, which may be inserted into a bone cavity or may be rigidly attachable to the tracking system construct, may be used to register the position of the tracking system. The ultrasound probe may be capable of transmitting and receiving data. The ultrasound probe is capable of detecting by way of non-limiting example, regions of relative bone density, for example between the less dense cancellous bone and the denser cortical bone. A shape such as a volume may be reconstructed by the ultrasound probe (or remote controller such as controller 120, FIG. 2) that visualizes the inner cortical wall relative to the ultrasound probe. Algorithmically the sampled shape or volume may be matched to the pre-operative data to infer the position of the probe relative to the bone. Because the probe is rigidly attached to the tracking system construct, it is possible to infer the position of the tracking system relative to the bone, i.e. operable to register the position of the tracking system from the readings of the ultrasound probe.

In another embodiment the ultrasound probe may be inserted into a bone cavity and used to register the bone position. The probe may be movable within the bone. The probe may be tracked with a camera or the position of the probe may be inferred algorithmically at each position reading. In another embodiment the ultrasound probe may be inserted into a bone cavity and used to generate pre-operative data for a surgical robotic system or surgical navigation system (also, computer aided surgical system). Many computer aided surgical systems rely on patient specific imaging to plan surgical procedures. This data may be generated from readings with an ultrasound probe inserted into a bone cavity.

The present technique employing patient specific bone jigs with imaging and/or minimal point sampling overcomes problems associated with current registration and tracking. To algorithmically identify anatomical structures is a non-trivial computational problem that may involve machine learning or complex geometric modelling techniques. Determining the pose or spatial position and orientation of an object is also challenging. In clinical practice, exposures are often small, and the features of a surgical site can be highly variable. Algorithmic feature detection with which to determine spatial orientation can prove a challenge. The availability of data on which to "train" or validate these algorithms is another major impediment to development. Conventional feature detection algorithms on which depth cameras rely, struggle correlating to models with small exposures with limited surface anomalies (smooth) in "noisy" environments (cartilage, blood, surgical tools and other soft tissues). Data sets of real-world procedures to train the algorithms are difficult to obtain. Furthermore, unlike spinal anatomy, identifying key anatomical landmarks with knees and hips in limited exposure can be quite challenging.

For example, the technique of the present disclosure may overcome the problems of conventional registration where a user sampling clinically known anatomical landmarks is subjective and prone to error. The present technique reduces the need in conventional registrations of having to sample a high number of points to increase accuracy, as increased sampling increases surgery time. Additionally, because the sampling of points requires a highly skilled user, such as a surgeon, it limits the ability of lower skilled users to support the task. Generating high accuracy registrations in a timely manner continues to be a challenge in the industry.

As may be recognized by those of ordinary skill in the art based on the teachings herein, numerous changes and modifications may be made to the above-described and other embodiments of the present invention without departing from the scope of the invention. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the invention be construed as including all such modifications and alterations.

The invention claimed is:

1. A surgical method comprising:

providing a robot comprising a robotic arm having an end effector, the robotic arm having a plurality of joints and plurality of body parts;

providing a controller comprising a memory, one or more processors in communication with the memory, and program instructions executable by the one or more processors via the memory to perform a method, the method comprising:

wirelessly obtaining reference data based on at least one camera of a wireless tracking device operably attached to a bone of a patient, the reference data associated with at least one of a plurality of markers, and the wireless tracking device comprising:

the at least one camera; and a wireless transmitter; and using the wirelessly obtained reference data based on the at least one camera of the wireless tracking device in a surgical navigation system to perform a surgical procedure on the patient; and wherein the plurality of markers is attached to the movable arm or joint of the robot.

2. The surgical method of claim 1, wherein the plurality of markers is attached to a surgical tool attached to a robot, a base of a robot, a cart, a fixture attached to a surgical table, surgical lighting, an outside-in navigation camera, and/or one or more objects in an operating room.

3. The surgical method of claim 1, wherein the using comprises updating a target position for a robot.

4. The surgical method of claim 1, wherein the wirelessly obtaining reference data comprises wirelessly obtaining a starting position, and wirelessly obtaining changes in a position from the starting position.

5. The surgical method of claim 1, wherein the using comprises:

using the reference data in the surgical navigation system to resect or excavate the bone of the patient based on a cut plan;

displaying an image representing the bone of the patient; and/or displaying an image representing a tool relative to the bone of the patient.

6. The surgical method of claim 1, further comprising obtaining or generating registrations data regarding registration of the wireless tracking device to the bone of the patient, and wherein the using comprises using the data regarding registration of the wireless tracking device to the bone of the patient and the obtained reference data in the surgical navigation system to perform the surgical procedure on the patient.

7. The surgical method of claim 1, further comprising generating data regarding registration of the wireless tracking device to the bone of the patient based on bone data of the bone of the patient and a secondary camera remote from the patient and the wireless tracking device.

8. The surgical method of claim 1, wherein:

the plurality of markers is attached to a robot having a stationary base and a robotic arm having a plurality of joints and plurality of body parts with at least one of the plurality of markers attached to the stationary base and at least one of the plurality of markers attached to one of the joints or body parts; and the reference data is associated with the stationary base and/or the at least one of the joints or body parts.

9. The surgical method of claim 1, wherein the plurality of markers comprises a plurality of movable markers, and wherein the plurality of movable markers is operably attached to a robot and/or to a plurality of tools attached to the robot.

10. The surgical method of claim 9, further comprising;

receiving intrinsic position data of the robot; and using the intrinsic position data to determine a position and orientation of the plurality of movable markers.

11. The surgical method of claim 9, further comprising;

providing a secondary camera;

tracking the robot with the secondary camera; and using the tracked robot to determine the location of the plurality of movable markers.

12. The surgical method of claim 1, further comprising:

wirelessly obtaining second reference data, the second reference data based on at least one camera of a second wireless tracking device operably attached to an object attached to the patient, the second reference data associated with at least one of the plurality of markers, and the second wireless tracking device comprising:

at least one camera; and a wireless transmitter; and using the first and second reference data in the surgical navigation system to perform the surgical procedure on the patient.

13. The surgical method of claim 12, wherein the object comprises a retractor.

14. The surgical method of claim 1, wherein the at least one camera of the wireless tracking device is pointed towards a robot arm and/or the at least one camera of the wireless tracking device is pointed towards a robot base.

15. The surgical method of claim 1, wherein the wireless tracking device further comprises an accelerometer and a gyroscope, and a magnetometer.

16. The surgical method of claim 1, wherein:

the wireless tracking device comprises;

the at least one camera;

an inertial measurement unit; and the wireless transmitter; and further comprising:

wirelessly obtaining position and orientation data, the position and orientation data based on the inertial measurement unit of the wireless tracking device operably attached to the bone of the patient; and the using comprises using the reference data and the position and orientation data in the surgical navigation system.

17. The surgical method of claim 1, wherein:

the wireless tracking device comprises:

the at least one camera comprising a plurality of cameras; and the wireless transmitter; and the reference data is based on the plurality of cameras of the wireless tracking device operably attached to the bone of the patient.

18. A surgical robotic system comprising:

a robot comprising a robotic arm having an end effector, the robotic arm having a plurality of joints and plurality of body parts; and a controller comprising a memory, one or more processors in communication with the memory, and program instructions executable by the one or more processors via the memory to perform the method of claim 1.

19. A computer program product comprising a non-transitory computer readable storage medium readable by a processing circuit and storing instructions for execution by the processing circuit for performing the method of claim 1.

20. A surgical method comprising:

providing a robot comprising a robotic arm having an end effector, the robotic arm having a plurality of joints and plurality of body parts;

providing a controller comprising a memory, one or more processors in communication with the memory, and program instructions executable by the one or more processors via the memory to perform a method, the method comprising:

wirelessly obtaining surface or structural data of a bone of a patient, the surface or structural data based on a probe of a wireless tracking device operably attached to the bone of the patient, and the wireless tracking device comprising:

the probe;

a wireless transmitter;

the wireless tracking device does not include a camera; and the probe comprises an ultrasound probe; and using the wirelessly obtained surface or structural data in a surgical navigation system to perform the surgical procedure on the patient.

21. The surgical method of claim 20, wherein the probe is inserted into a cavity in the bone of the patient.

22. The surgical method of claim 20, further comprising obtaining or generating registration data of the probe operably attached to the bone, and wherein the using comprises using the surface or structural data and registration data in the surgical navigation system.

23. The surgical method of claim 20, wherein the wireless transmitter further comprises an internal measurement unit, and further comprising:

wirelessly obtaining position and orientation data, the position and orientation data based on the inertial measurement unit of the wireless tracking device operably attached to the bone of the patient; and wherein:

the using comprises using the surface or structural data and the position and orientation data in the surgical navigation system to perform the surgical procedure on the patient.

24. The surgical method of claim 20, wherein the wireless tracking device further comprises at least one camera, and further comprising:

wirelessly obtaining reference data based on the at least one camera of the wireless tracking device operably attached to the bone of the patient; and wherein:

the using comprises using the surface or structural data and the reference data in the surgical navigation system to perform the surgical procedure on the patient.

25. A computer program product comprising a non-transitory computer readable storage medium readable by a processing circuit and storing instructions for execution by the processing circuit for performing the method of claim 20.

* * * * *